United States Patent
Iida et al.

(10) Patent No.: US 8,541,009 B2
(45) Date of Patent: Sep. 24, 2013

(54) COSMETIC

(75) Inventors: Masayuki Iida, Tokyo (JP); Takamasa Yamamoto, Tokyo (JP); Yuko Yago, Tokyo (JP)

(73) Assignee: Kao Corporation, Tokyo (JP)

( * ) Notice: Subject to any disclaimer, the term of this patent is extended or adjusted under 35 U.S.C. 154(b) by 189 days.

(21) Appl. No.: 12/997,443

(22) PCT Filed: Jun. 11, 2009

(86) PCT No.: PCT/JP2009/002656
§ 371 (c)(1),
(2), (4) Date: Dec. 10, 2010

(87) PCT Pub. No.: WO2009/150846
PCT Pub. Date: Dec. 17, 2009

(65) Prior Publication Data
US 2011/0104222 A1    May 5, 2011

(30) Foreign Application Priority Data
Jun. 11, 2008    (JP) .................. 2008-152456

(51) Int. Cl.
*A61K 8/02* (2006.01)
*A61K 8/00* (2006.01)
*A61K 8/18* (2006.01)

(52) U.S. Cl.
USPC ................ 424/401; 424/69; 424/63

(58) Field of Classification Search
USPC ............................. 424/401, 63, 69
See application file for complete search history.

(56) References Cited

U.S. PATENT DOCUMENTS

| | | | |
|---|---|---|---|
| 5,578,311 A * | 11/1996 | Nagatani et al. ............... | 424/401 |
| 6,280,748 B1 | 8/2001 | Morita et al. | |
| 7,153,573 B2 * | 12/2006 | Tsuji et al. .................... | 428/403 |
| 2004/0071956 A1 | 4/2004 | Tsuji et al. | |
| 2005/0008597 A1 * | 1/2005 | Furukawa et al. .......... | 424/70.12 |
| 2006/0030686 A1 | 2/2006 | Lion | |
| 2008/0003195 A1 | 1/2008 | Arnaud et al. | |

FOREIGN PATENT DOCUMENTS

| | | |
|---|---|---|
| CN | 1488666 A | 4/2004 |
| EP | 0 872 228 A1 | 10/1998 |
| JP | 63 139106 | 6/1988 |
| JP | 8 12526 | 1/1996 |
| JP | 9 202714 | 8/1997 |
| JP | 9 227331 | 9/1997 |
| JP | 10-113370 | 5/1998 |
| JP | 11 349442 | 12/1999 |
| JP | 2000 63225 | 2/2000 |
| JP | 2000 86429 | 3/2000 |
| JP | 2003 226611 | 8/2003 |
| JP | 2004-196719 | 7/2004 |
| JP | 2004 203768 | 7/2004 |
| JP | 2004 277289 | 10/2004 |
| JP | 2006-37109 A | 2/2006 |
| JP | 2006 56861 | 3/2006 |
| JP | 2007 1868 | 1/2007 |
| JP | 2007 39371 | 2/2007 |
| JP | 2007 320960 | 12/2007 |
| JP | 2007 332295 | 12/2007 |
| WO | WO 03/045337 A2 | 6/2003 |

OTHER PUBLICATIONS

Office Action issued Jun. 14, 2012 in Chinese Application No. 200980121277.7 (With English Translation).
International Search Report issued Sep. 15, 2009 in PCT/JP09/002656 filed Jun. 11, 2009.
Office Action issued Jan. 25, 2013 in Chinese Patent Application No. 200980121277.7 (with English translation).

* cited by examiner

*Primary Examiner* — Blessing Fubara
*Assistant Examiner* — Jennifer Berrios
(74) *Attorney, Agent, or Firm* — Oblon, Spivak, McClelland, Maier & Neustadt, L.L.P.

(57) ABSTRACT

A cosmetic composition contains the following components (A), (B) and (C):
(A) from 0.1 to 30 wt. % of a vinyl-based polymer having a carbosiloxane dendrimer structure in a side chain thereof,
(B) from 0.1 to 30 wt. % of a nonvolatile cosmetic oil, which is in a liquid form at 25° C. and has a solubility parameter of 16.5 or greater, and
(C) from 0.1 to 30 wt. % of a hydrophobic powder, and a weight ratio of the component (A) to the component (B), (A)/(B), is from 0.3 to 5.

9 Claims, No Drawings

COSMETIC

CROSS REFERENCE TO RELATED APPLICATION

This application is a 371 of PCT/JP09/02656, filed on Jun. 11, 2009, and claims priority to Japanese Patent Application No. 2008-152456, filed on Jun. 11, 2008.

FIELD OF THE INVENTION

The present invention relates to a cosmetic composition.

BACKGROUND OF THE INVENTION

In recent years, there have been required emulsified cosmetic compositions for makeup, which have good spreadability to prevent uneven application, to give a natural finish while covering imperfections like uneven pigmentation such as blemishes, freckles or skin dullness and/or skin roughness such as pores or wrinkles.

To cover roughness such as pores with a natural finish, there have conventionally been proposed a cosmetic composition making combined use of a composite powder, which is composed of different species of organopolysiloxanes, and an acrylate-silicone graft copolymer (Patent Document 1), an oil-in-water emulsified cosmetic composition making combined use of a crosslinked methylpolysiloxane and a spherical powder (Patent Document 2), and a cosmetic composition containing a translucent spherical powder, a silicone and water (Patent Document 3), and so on. However, these cosmetic compositions are poor in spreadability or are sticky in some instances and are not fully satisfactory from the standpoint of feel upon use, because they are intended to form a thick film on the skin and to prevent a film from thinly spreading to excess on the skin.

On the other hand, emulsified cosmetic compositions with a low viscosity, which can provide a good feel upon use, are good in spreadability, so that their cosmetic films tend to become thin. It is, therefore, a common practice to have a powder of high refractive index adhered evenly on the skin by using a film forming agent in combination with the powder. The addition of the film forming agent in a large content, however, results in poor spreadability and stickiness. Further, use of a film forming agent with high adhesion involves a problem in that a sense of discomfort such as a film feeling or a tight feel may be experienced in the skin after its application.

Moreover, these methods are all accompanied by another problem in that, although such conventional cosmetics are excellent in the adhesion to the skin immediately after finishing, they are low in anti-sebum properties or skin followability, and therefore, pores become noticeable with time or rough skin become visible as a result of creasing or being caught in wrinkles.

It is known that, when a vinyl-based polymer having a carbosiloxane dendrimer structure in a side chain thereof is used, a firm cosmetic film is formed to achieve improvements in the long-lasting property of makeup such as anti-sebum properties and abrasion resistance (Patent Document 4, Patent Document 5).

PRIOR ART DOCUMENTS

Patent Documents

[Patent Document 1] JP-A-2000-86429
[Patent Document 2] JP-A-2007-39371
[Patent Document 3] JP-A-11-349442
[Patent Document 4] JP-A-2000-63225
[Patent Document 5] JP-A-2003-226611

SUMMARY OF THE INVENTION

Problem to be Solved by the Invention

Such vinyl-based polymers form very hard films, and therefore, are excellent against physical action such as friction. Nonetheless, they have problems in skin followability and film feeling because their films are hard.

The present invention is to provide a cosmetic composition, which has good spreadability and low stickiness, provides a feel upon use with a little sense of discomfort such as film feeling, is excellent in the effect that makes rough skin parts such as pores hardly visible, and makes roughness, such as fine wrinkles and pores, hardly visible or hardly forms creases, with time.

Means for Solving the Problem

The present inventors have found that the combined use of a vinyl-based polymer, which has a carbosiloxane dendrimer structure in a side chain thereof, a hydrophobic powder and a particular nonvolatile cosmetic oil in specific proportions makes it possible to obtain a cosmetic which can provide a good feel upon use, can form an even cosmetic film on the skin, gives a low film feeling after being applied to the skin, has high adhesion to the skin, and is excellent in the effect that makes fine wrinkles and pores hardly visible.

The present invention provides a cosmetic containing the following components (A), (B) and (C):

(A) from 0.1 to 30 wt. % of a vinyl-based polymer having a carbosiloxane dendrimer structure in a side chain thereof, (B) from 0.1 to 30 wt. % of a nonvolatile cosmetic oil, which is in a liquid form at 25° C. and has a solubility parameter of 16.5 or greater, and (C) from 0.1 to 30 wt. % of a hydrophobic powder, wherein a weight ratio of the component (A) to the component (B), (A)/(B), is from 0.3 to 5.

Effects of the Invention

The cosmetic composition according to the present invention has high stability, good spreadability and low stickiness, provides a feel upon use with a little sense of discomfort such as film feeling, and is excellent in the effect that makes skin roughness such as pores hardly visible. In addition, the cosmetic composition is good in the long-lasting property of makeup, and makes roughness such as fine wrinkles and pores hardly visible, or hardly forms creases, with time.

In general, an adhesive can be obtained by adding a tackifier, which is a resin of low molecular weight and high glass transition point such as rosin, or a plasticizer, which is a substance of low molecular weight and low glass transition point, to a rubbery substance or polymer resin having no tackiness by itself. In the case of an acrylic or methacrylic polymer formed from a monomer having a linear polydimethylsiloxane in a side chain thereof, the polymer itself shows tackiness. On the other hand, a vinyl-based polymer having a carbosiloxane dendrimer structure in a side chain thereof is in the form of a hard resin and does not show tackiness. When the vinyl-based polymer having the carbosiloxane dendrimer structure in a side chain thereof is combined with a nonvolatile cosmetic oil having a solubility parameter of 16.5 or greater, however, the vinyl-based polymer having the carbosiloxane dendrimer structure in a side chain thereof is plasticized so that it becomes soft and moreover, shows adhesiveness. Liquid oil having the solubility parameter in the above-described range, therefore, acts as a plasticizer. It is, accordingly, considered that, as their mixture forms films having tackiness, the adhesive force to the skin and powder is improved, and as a whole cosmetic film, the adhesive properties to the skin are increased and the followability to the skin is improved.

DETAILED DESCRIPTION OF THE INVENTION

In the vinyl-based polymer having the carbosiloxane dendrimer structure in a side chain thereof which is useful as the component (A) in the present invention, the carbosiloxane dendrimer structure may preferably be a group represented by the following formula (1):

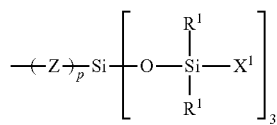
(1)

wherein Z is a divalent organic group, p is 0 or 1, $R^1$ is an alkyl group having from 1 to 10 carbon atoms or an aryl group, and $X^1$ is a silylalkyl group which, when i=1, is represented by the following formula:

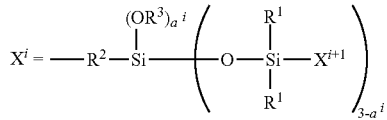

wherein $R^1$ is the same as defined above, $R^2$ is an alkylene group having from 2 to 10 carbon atoms, $R^3$ is an alkyl group having from 1 to 10 carbon atoms, $X^{i+1}$ is a hydrogen atom or a group selected from the group consisting of an alkyl group having from 1 to 10 carbon atoms, an aryl group and the silylalkyl group, i is an integer of from 1 to 10 which represents the generation of the silylalkyl group, and $a^i$ is an integer of from 0 to 3.

In the formula (1), Z is a divalent organic group, and alkylene groups, arylene groups, aralkylene groups, ester-containing divalent organic groups, ether-containing divalent organic groups, ketone-containing divalent organic groups, and amido-containing divalent organic groups can be exemplified. Of these, organic groups represented by the following formulas are preferred.

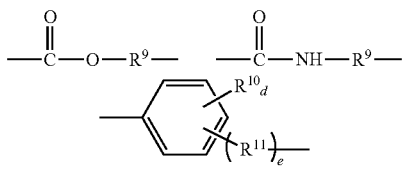

In these formulas, $R^9$ is an alkylene group having from 1 to 10 carbon atoms, and methylene, ethylene, propylene and butylene can be exemplified. Of these, ethylene and propylene are preferred. $R^{10}$ is an alkyl group having from 1 to 10 carbon atoms, and methyl, ethyl, propyl and butyl can be exemplified. Of these, methyl is preferred. $R^{11}$ is an alkylene group having from 1 to 10 carbon atoms, and alkylene groups such as methylene, ethylene, propylene and butylene can be exemplified. Of these, ethylene is preferred. d is an integer of from 0 to 4, and e is 0 or 1.

In the formula (1), $R^1$ is an alkyl group having from 1 to 10 carbon atoms or an aryl group. As the alkyl group, methyl, ethyl, propyl, butyl, pentyl, isopropyl, isobutyl, cyclopentyl and cyclohexyl can be exemplified. As the aryl group, phenyl and naphthyl can be exemplified. Of these, methyl and phenyl are preferred, with methyl being more preferred.

$X^1$ is a silylalkyl group which, when i=1, is represented by the following formula:

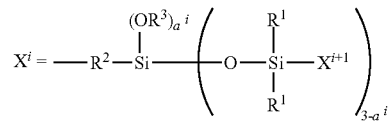

In the formula, $R^1$ is the same as defined above. $R^2$ is an alkylene group having from 2 to 10 carbon atoms, and there can be exemplified linear alkylene groups such as ethylene, propylene, butylene and hexylene, and branched alkylene groups such as methylmethylene, methylethylene, 1-methylpentylene and 1,4-dimethylbutylene. Of these, ethylene, methylethylene, hexylene, 1-methylpentylene and 1,4-dimethylbutylene are preferred. $R^3$ is an alkyl group having from 1 to 10 carbon atoms, and methyl, ethyl, propyl, butyl and isopropyl can be exemplified. $X^{i+1}$ is a hydrogen atom or a group selected from the group consisting of an alkyl group having from 1 to 10 carbon atoms, an aryl group and the above-described silylalkyl group. $a^i$ is an integer of from 0 to 3. i is an integer of from 1 to 10 which represents the generation of the silylalkyl group, in other words, the number of repetition of the silylalkyl group.

Preferred as the component (A), i.e., the vinyl-based polymer is a vinyl-based polymer, which has a carbosiloxane dendrimer structure and is obtained by (co)polymerizing the following components (A1) and (A2):

(A1) from 0 to 99.9 weight parts of a vinyl monomer other than that to be described in (A2), and (A2) from 100 to 0.1 weight parts of a carbosiloxane dendrimer having a radical-polymerizable organic group and represented by the following formula (2):

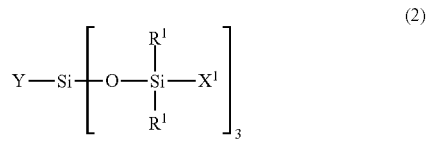
(2)

wherein Y is the radical-polymerizable organic group, and $R^1$ and $X^1$ are the same as defined above.

In the above-described formula, Y is the radical-polymerizable organic group, and $R^1$ is an alkyl group having from 1 to 10 carbon atoms or an aryl group. As the alkyl group, methyl, ethyl, propyl, butyl, pentyl, isopropyl, isobutyl, cyclopentyl and cyclohexyl can be exemplified. As the aryl group, phenyl and naphthyl can be exemplified. Of these, methyl and phenyl are preferred, with methyl being more preferred.

In this vinyl-based polymer, the component (A1), i.e., the vinyl monomer can be any vinyl monomer insofar as it contains a radical-polymerizable vinyl group, and no limitation is imposed on its kind. Examples of such a vinyl monomer include lower alkyl (meth)acrylates such as methyl (meth) acrylate, ethyl (meth) acrylate, n-propyl (meth)acrylate, isopropyl (meth)acrylate, n-butyl (meth)acrylate, isobutyl (meth)acrylate, tert-butyl (meth)acrylate, n-hexyl (meth)acrylate, and cyclohexyl (meth)acrylate; higher alkyl (meth)acrylates such as 2-ethylhexyl (meth)acrylate, octyl (meth) acrylate, lauryl (meth)acrylate, and stearyl (meth)acrylate; fatty acid vinyl esters such as vinyl acetate, vinyl propionate, vinyl butyrate, vinyl caproate, vinyl 2-ethylhexanoate, vinyl laurate, and vinyl stearate; aromatic-containing monomers such as styrene, vinyltoluene, benzyl (meth)acrylate, and phenoxyethyl (meth)acrylate; amido-containing vinyl monomers such as (meth)acrylamide, N-methylol (meth)acrylamide, N-methoxymethyl(meth)acrylamide, isobutoxymethoxy(meth)acrylamide, N,N-dimethyl(meth)acrylamide, vinylpyrrolidone, and N-vinylacetamide; hydroxyl-containing vinyl monomers such as hydroxyethyl (meth)acrylate, hydroxypropyl (meth)acrylate, glyceryl (meth)acrylate, and hydroxyethyl acrylamide; carboxyl-containing vinyl monomers such as (meth)acrylic acid, itaconic acid, crotonic acid, fumaric acid and maleic acid, and salts thereof; ether-bond-containing vinyl monomers such as tetrahydrofurfuryl (meth)acrylate, butoxyethyl (meth)acrylate, ethoxy diethylene glycol (meth)acrylate, polyethylene glycol (meth)acrylate, polypropylene glycol mono (meth)acrylate, hydroxybutyl vinyl ether, cetyl vinyl ether, and 2-ethylhexyl vinyl ether; reactive-group-containing monomers such as glycidyl (meth)acrylate, (meth)allyl glycidyl ether, methacryloyloxyethyl isocyanate, and (meth)acryloxypropyl trimethoxysilane; macromonomers such as polydimethylsiloxane containing a (meth)acryl group at one end thereof, and polydimethylsiloxane containing a styryl group at one end thereof; butadiene; vinyl chloride; vinylidene chloride; (meth)acrylonitrile; dibutyl fumarate; maleic anhydride; sulfonic-containing, radical-polymerizable, unsaturated monomers such as styrene sulfonic acid, and acrylamido-2-methylpropanesulfonic acid, and alkali metal salts, ammonium salts and organic amine salts thereof; quaternary ammonium salts derived from (meth)acrylic acid such as 2-hydroxy-3-methacryloxypropyl trimethylammonium chloride; methacrylate esters of alcohols having a tertiary amino group such as diethylaminoethyl methacrylate; and vinylpyridine, and quaternary ammonium salts thereof.

In addition, polyfunctional vinyl monomers are also usable. Examples include trimethylolpropane tri(meth)acrylate, pentaerythritol tri(meth)acrylate, ethylene glycol di(meth)acrylate, tetraethylene glycol di(meth)acrylate, polyethylene glycol di(meth)acrylate, 1,4-butanediol di(meth)acrylate, 1,6-hexanediol di(meth)acrylate, neopentyl glycol di(meth)acrylate, trimethylolpropanetrioxyethyl (meth)acrylate, tris(2-hydroxyethyl)isocyanurate di(meth)acrylate, tris(2-hydroxyethyl)isocyanurate tri(meth)acrylate, and unsaturated-group-containing silicone compounds such as styryl-capped polydimethylsiloxane.

No limitation is imposed on the kind or the like of the carbosiloxane dendrimer as the component (A2), insofar as it is one containing a radical-polymerizable organic group and represented by the formula (2). In the formula (2), Y is a radical-polymerizable organic group, and can be any radically-reactable organic group. Specifically, (meth)acryloxy-containing organic groups, (meth)acrylamido-containing organic groups and styryl-containing organic groups, which are represented by the below-described formulas, respectively, alkenyl groups having from 2 to 10 carbon atoms, and the like can be mentioned.

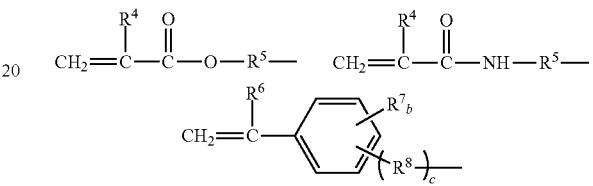

wherein $R^4$ and $R^6$ are each a hydrogen atom or methyl group, $R^5$ and $R^8$ are each an alkylene group having from 1 to 10 carbon atoms, and $R^7$ is an alkyl group having from 1 to 10 carbon atoms, b is an integer of from 0 to 4, and c is 0 or 1.

Examples of such a radical-polymerizable organic group include 2-acryloyloxyethyl, 3-acryloyloxypropyl, 2-methacryloyloxyethyl, 3-methacryloyloxypropyl, 4-vinylphenyl, 3-vinylphenyl, 4-(2-propenyl)phenyl, 3-(2-propenyl)phenyl, 2-(4-vinylphenyl)ethyl, 2-(3-vinylphenyl)ethyl, vinyl, allyl, methallyl, and 5-hexenyl.

When i=1, that is, the number of generation of the silylalkyl group is 1 in the formula (2), the carbosiloxane dendrimer as the component (A2) is represented by the following formula:

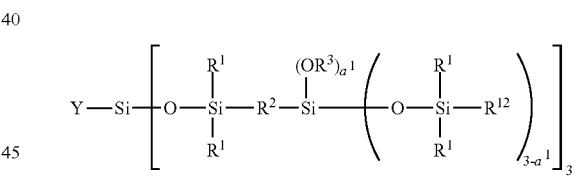

wherein Y, $R^1$, $R^2$ and $R^3$ are the same as defined above, $R^{12}$ is a hydrogen atom or the same as $R^1$, $a^1$ is the same as $a^i$, and the average total number of $a^i$ in a molecule is from 0 to 7.

As such a carboxydendrimer (A2) with a radical-polymerizable organic group contained therein, carbosiloxane dendrimers represented by the following average composition formulas can be exemplified.

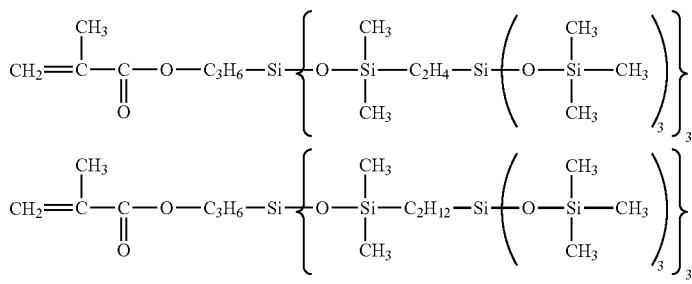

-continued
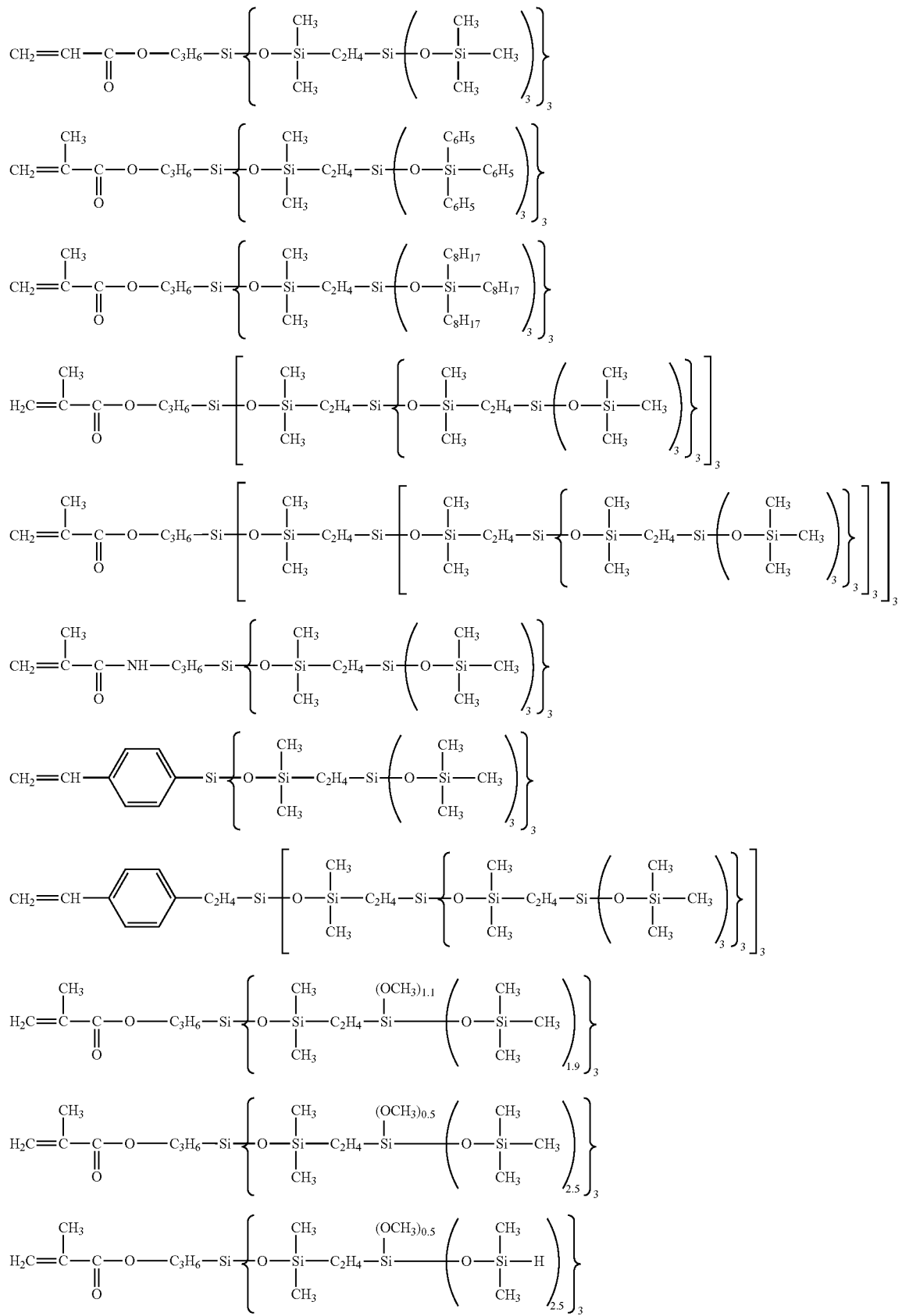

-continued

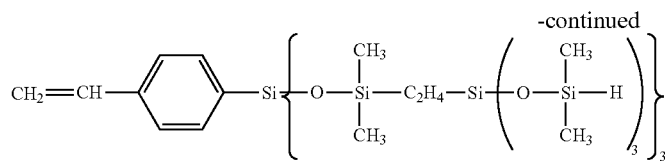

Such carbosiloxane dendrimers can be produced, for example, according to the production procedure described in JP-A-11-1530, JP-A-2000-63225 or the like.

In the vinyl-based polymer useful in the present invention and containing the dendrimer structure, the weight ratio of the component (A1) to the component (A2), (A1):(A2), may be in a range of preferably from 0:100 to 99.9:0.1, more preferably from 5:95 to 90:10, even more preferably from 10:90 to 80:20.

The number average molecular weight of the vinyl-based polymer having the carbosiloxane dendrimer structure which is useful as the component (A) in the present invention may be preferably from 3,000 to 2,000,000, more preferably from 5,000 to 800,000 from the standpoint of ease of its addition as a cosmetic raw material. Its form can be any one of liquid form, gum form, paste form, solid form and the like at room temperature, with a solid form being preferred from the viewpoint of the long-lasting property of the resulting cosmetic film. From the viewpoint of its compatibility in the cosmetic, a solution or dispersion of the vinyl-based polymer diluted in a solvent is preferred.

As the vinyl-based polymer having the carbosiloxane dendrimer structure in a side chain thereof, a silicone dendrimer-acrylate copolymer is preferred. Commercial products such as "FA4001CM" (decamethylcyclopentasiloxane solution) and "FA4002ID" (isododecane solution) (both, products of Dow Corning Toray Silicone Co., Ltd.) can be used.

As the component (A), one or more vinyl-based polymers can be used. The component (A) is contained at from 0.1 to 30 wt. %, preferably 0.5 to 20 wt. % in the whole composition. A content of lower than 0.1 wt. % leads to low adhesion, while a content of greater than 30 wt. % results in reduced spreadability as a feel upon use.

The component (B), i.e., the nonvolatile cosmetic oil is in a liquid form at 25° C. The term "liquid form" as used herein means to have flowability, and therefore, the nonvolatile cosmetic oil includes one having a cream form or paste form. Further, the term "nonvolatile" means a weight reduction rate of 1% or smaller after left at 25° C. and under a normal pressure for 24 hours. The molecular weight of the nonvolatile cosmetic oil as the component (B) may be in a range of preferably from 250 to 2,000, more preferably from 300 to 1,000. A molecular weight lower than this range tends to result in diffusion, while a molecular weight higher than this range may lead to a reduction in the compatibility with the component (A) so that the plasticizing effect may become hardly available.

Further, the nonvolatile cosmetic oil as the component (B) has a solubility parameter (SP value) of 16.5 or greater, preferably from 17.5 to 23, more preferably from 19 to 22. A nonvolatile cosmetic oil having the SP value which falls within this range is compatible with the vinyl-based polymer having the carbosiloxane dendrimer structure in a side chain thereof, and develops tackiness. As the solubility parameter is significantly different from the solubility parameter (about 15) of a low-viscosity silicone oil such as polydimethylsiloxane, the nonvolatile cosmetic oil is incompatible with the low-viscosity silicone oil and does not reduce the strength and adhesive properties of a cosmetic film.

The term "SP value" of a cosmetic oil is a solubility parameter $\delta$, and is a material constant expressed by $\delta=(E/V)^{1/2}(J/cm^3)$ in which E is the molecular aggregation energy of the liquid and V is the molecular volume of the liquid. SP values can be determined by various methods. In the present invention, however, they were determined in accordance with the Fedors method by using the parameters described in Items VII685 to 686 of J. BRANDRUP: "POLYMER HANDBOOK $4^{th}$" JOHN WILEY & SONS, INC. (published in 1999).

Specific examples include polar cosmetic oils such as isotridecyl isononanoate (16.5), diisostearyl malate (17.9), isostearyl myristate (16.9), triisostearin (17.1), tris-ethoxydiglycol phosphate (18.1), neopentylglycol dicaprate (18.2), glyceryl tri(2-ethylhexanoate) (18.6), diglyceryl diisostearate (18.7), glyceryl monoisostearate monomyristate (19.1), 2-ethylhexyl paramethoxycinnamate (19.2), dl-α-tocopherol (19.4), methylphenylpolysiloxane (20.0), and diglyceryl monoisostearate (21.7).

These nonvolatile cosmetic oils can be used either singly or in combination, and can be contained at from 0.1 to 30 wt. %, preferably from 0.5 to 20 wt. % in the whole composition. A content of lower than 0.1 wt. % cannot obtain sufficient effects, while a content of greater than 30 wt. % results in a deteriorated feel upon use such as heavier spreading or stickiness.

It is more preferred to use two or more cosmetic oils in combination. From the standpoints of the feel of use, the long-lasting property of makeup and the stability of the composition, it is even more preferred to combine a cosmetic oil having the SP value which is in the range of from 16.8 to 18.4, and another cosmetic oil having the SP value which is in the range of from 18.5 to 23, at a ratio of from 0.01 to 100.

The weight ratio of the component (A) to the component (B), (A)/(B), is from 0.3 to 5, with from 0.5 to 4 being more preferred and from 1.2 to 3 being even more preferred. A weight ratio of greater than 5 has tendency of failing to obtain sufficient tackiness and resulting in reduced followability to the skin. A weight ratio of smaller than 0.3, on the other hand, has tendency of also failing to obtain sufficient tackiness and moreover, resulting in a deteriorated feel upon use such as stickiness.

The hydrophobic powder useful as the component (C) in the present invention is a powder that shows hydrophobicity, and includes a powder having hydrophobicity by itself and also a powder that is not hydrophobic by itself but has been subjected to hydrophobic treatment to show hydrophobicity. No limitation is imposed depending on its shape such as spherical shape, plate shape or needle shape; its particle size such as fumed form (several nanometers to several tens nanometers), fine particles (several tens nanometers to several hundreds nanometers) or pigment grade (several hundreds nanometers to several micrometers); its particle structure such as porous structure or nonporous structure; or the like.

Specific examples of the powder having hydrophobicity by itself include nylon powder, polymethyl methacrylate, powder of acrylonitrile-methacrylic acid copolymer, powder of vinylidene chloride-methacrylic acid copolymer, polyethylene powder, polystyrene powder, organopolysiloxane elastomer powder, polymethylsilsesquioxane powder, polytetrafluoroethylene powder, urethane powder, wool powder, magnesium stearate, zinc stearate, N-acyl lysine, organically-modified clay materials, boron nitride, and organic tar pigments.

Specific examples of the powder that is not hydrophobic by itself include titanium dioxide, Prussian blue, ultramarine, red iron oxide, yellow iron oxide, black iron oxide, zinc oxide, aluminum oxide, silicon dioxide, magnesium oxide, zirconium oxide, magnesium carbonate, calcium carbonate, chromium oxide, chromium hydroxide, aluminum silicate, magnesium silicate, aluminum magnesium silicate, mica, synthetic mica, synthetic sericite, sericite, talc, kaolin, barium sulfate, bentonite, smectite, and bismuth oxychloride; and composite powders such as titanated mica, iron-oxide-coated mica, iron-oxide-coated titanated mica, fine-particulate titanium dioxide-coated titanated mica, fine-particulate zinc-oxide-coated titanated mica, red-iron-oxide-coated titanated mica, barium-sulfate-coated titanated mica, titanium dioxide-containing glass flakes, and zinc-oxide-containing silicon dioxide.

When subjecting a powder, which is not hydrophobic by itself, to hydrophobization treatment, a known hydrophobizing agent can be used in a known hydrophobizing method. For example, dry treatment, wet treatment or the like can be conducted using a surface treatment agent such as a fluorine compound, a silicone-based compound, a metallic soap, a cosmetic oil, or the like. Specific examples of the surface treatment agent include fluorine-containing compounds such as perfluoroalkylphosphate esters and perfluoroalkylalkoxysilanes, silicone-based compounds such as methylhydrogenpolysiloxane, cyclic silicones and organopolysiloxanes modified with a trialkoxy group at one or both ends thereof, metallic soaps such as aluminum stearate and zinc stearate, and amino-acid-based compounds such as lauroyl lysine. The amount of surface treatment may preferably be, but is not limited to, from 0.5 to 20 wt. %, with from 2 to 8 wt. % being more preferred, based on the powder to be subjected to the surface treatment.

As the component (C), i.e., the hydrophobic powder, one or more hydrophobic powders can be used. The component (C) is contained at from 0.1 to 30 wt. %, with from 1 to 25 wt. % being preferred and from 5 to 20 wt. % being more preferred, in the whole composition.

Among hydrophobic powders, spherical powders have property that reduces regular reflection and/or irregular reflection, and their shapes include true sphere, approximate sphere and spheroid. In addition, spherical powders having concavities and convexities on their surfaces are also included. When a spherical powder has an average particle size of from 1 to 20 µm, the spherical powder is not buried in a cosmetic film, and moreover, tends to evenly adhere to rough parts. The spherical powder, therefore, can fully show "obscurement" effects, that is, effects that obscure the boundaries of roughness such as pores and fine wrinkles to make them hardly visible. By controlling the average particle size of a spherical powder to 1 µm or greater, the spherical powder is not buried in a cosmetic film and can provide a smooth and good feel upon use.

Specific examples of such spherical powders include metal oxides such as spherical $SiO_2$ and $Al_2O_3$, inorganic compounds such as barium sulfate and calcium carbonate, and high molecular compounds such as polyethylene, polymethyl methacrylate, polystyrene, nylon, cellulose, silicone resins and polyurethanes. Spherical powders can be used either singly or in combination as a mixture.

The inclusion of from 0.5 to 15 wt. %, preferably from 1 to 10 wt. % of a plate powder having an average particle size of from 1 to 15 µm and from 0.5 to 15 wt. %, preferably from 1 to 10 wt. %, of a spherical powder having an average particle size of from 1 to 20 µm as the hydrophobic powder is preferred, because a sensation of glossiness can be imparted without impairment to a natural finish with a feel of bare skin or a feel of transparency. In addition, effect to conceal pore/roughness can be obtained. It is to be noted that the term "average particle size" as used herein means a volume-basis average particle size as measured by employing a laser diffraction particle size distribution analyzer while using ethanol as a solvent.

The plate powder adheres to smooth parts of the skin to give a sensation of glossiness, while the spherical powder adheres to rough parts to make the rough parts hardly visible. If the average particle size of the plate powder is greater than 15 µm, its glossiness is so high that a sensation of garishness is strong, a finish tends to become unnatural and over-shiny, the retention of a makeup is poor, and pores become more visible. Therefore, such a large average particle size is not preferred. Specific examples of such a plate powder include clay minerals such as mica, talc and sericite; and composite powders such as titanated mica, iron-oxide-coated mica, iron-oxide-coated titanated mica, fine-particulate titanium dioxide-coated titanated mica, fine-particulate zinc-oxide-coated titanated mica, red-iron-oxide-coated titanated mica, barium-sulfate-coated titanated mica, titanium dioxide-containing glass flakes, and zinc-oxide-containing silicon dioxide. These plate powders can be used either singly or in combination as needed.

Among such hydrophobic powders, those containing a color pigment are useful especially as makeup cosmetics such as foundations, cheek colors and eye shadows. No limitation is imposed on such a color pigment insofar as it is commonly used in cosmetics. Examples include inorganic pigments such as titanium dioxide, cerium oxide, aluminum oxide, yellow iron oxide, black iron oxide, red iron oxide, Prussian blue and ultramarine; and organic pigments such as Yellow No. 4 (Tartrazine), Yellow No. 5 (Sunset Yellow FCF), Yellow No. 401 (Hanza Yellow), Red No. 226 (Helindone Pink CN), Red No. 201 (Lithol Rubine B), Red No. 202 (Lithol Rubine BCA), Blue No. 1 (Brilliant Blue FCF) and Blue No. 404 (Phthalocyanine Blue). In addition, composite pigments such as titanium dioxide coated or combined with silicic acid anhydride and iron oxides coated with polymers can also be used.

As the color pigment, the above-exemplified color pigments can be used either singly or in combination. The color pigment may be contained at preferably from 0.1 to 30 wt. %, more preferably from 1 to 10 wt. % in the whole composition, because blemishes and freckles are hardly visible, the covering power is excellent, and the feel upon use is good.

As the color pigment or plate powder, it is preferred to contain an iron oxide or an iron-oxide-coated powder. The iron oxide can be any one of red iron oxide, yellow iron oxide, black iron oxide and the like, and the iron-oxide-coated powder can be iron-oxide-coated mica, iron-oxide-coated titanated mica, iron-oxide-coated synthetic bronze mica, iron-oxide-coated glass flakes, iron-oxide-enclosing glass flakes or the like.

As a colorant presenting a hue of red, black or yellow or by changing the intensity and tone of pearlescence of a scaly powder, iron oxide is an important component for exhibiting the basic performance of a foundation or the like. Once such a powder falls off, aggregates or becomes uneven and the makeup is disturbed, on the other hand, the makeup can be hardly touched up and fixed.

No limitation is imposed on the average particle size of the above-described powder component. In the cosmetic according to the present invention, however, the content of particles of 2 μm and smaller may range preferably from 0.1 to 20 wt. %, more preferably from 0.1 to 15 wt. % because an excellent feel upon use is available. It is to be noted that the term "average particle size" as used herein means a volume-basis average particle size as measured by employing a laser diffraction particle size distribution analyzer while using ethanol as a solvent.

The cosmetic according to the present invention may further contain (D) a polyether-modified silicone. The inclusion of the polyether-modified silicone facilitates the fixing of makeup, and therefore, is preferred.

A polyether-modified silicone is dimethylpolysiloxane with one or more polyoxyalkylene groups, preferably polyoxyethylene groups or poly(oxyethylene/oxypropylene) groups bonded thereto. Polyether-modified silicones having various bonding positions, HLBs and viscosities are known. As the bonding positions, those modified at side chain, one end or both ends of the silicone chains are known. Further, those containing one or more silicone chains and one or more polyoxyalkylene chains linked together as blocks in their backbones are also known. In the present invention, such polyether-modified silicones are all usable irrespective of the bonding positions, and those of the side-chain modified type or block copolymer type are preferred.

In terms of HLB, those of from 1 to 6 are preferred, with those of from 2 to 5 being more preferred. HLB is defined by the Griffin's method. In terms of viscosity, those of from 20 to 100,000=$^2$/sat 25° C. are preferred, with those of from 50 to 50,000 mm$^2$/s at 25° C. being more preferred. As a viscosity, a viscosity value (mPa·s) when measured for 1 minute by a Brookfield Viscometer under the conditions of No. 1 rotor and 60 rpm (for viscosities of lower than 100 mm$^2$/s), No. 2 rotor and 30 rpm (for viscosities of not lower than 100 mm$^2$/s but lower than 1,000 mm$^2$/s), No. 3 rotor and 12 rpm (for viscosities of not lower than 1,000 mm$^2$/s but lower than 10,000 mm$^2$/s), or No. 4 rotor and 6 rpm (for viscosities of not lower than 10,000 mm$^2$/s) is reworded, as it is, as a kinematic viscosity (mm$^2$/s).

Specific examples of such polyether-modified silicones include "SILICONE KF-6015" (HLB: 4.5, viscosity: 150 mm$^2$/s), "SILICONE KF-6017" (HLB: 4.5, viscosity: 600 mm$^2$/s, Shin-Etsu Chemical Co., Ltd.), "SILICONE KF-6019" (HLB: 4.5, viscosity: 850 mm$^2$/s, Shin-Etsu Chemical Co, Ltd.), "SILICONE KF-6028" (HLB: 4.5, viscosity: 900 mm$^2$/s, Shin-Etsu Chemical Co., Ltd.), "SILICONE SH-3772M" (HLB: 6, viscosity: 1,050 mm$^2$/s, Dow Corning Toray Co., Ltd.), "SILICONE SH-3775M" (HLB: 5, viscosity: 1,600 mm$^2$/s, Dow Corning Toray Co., Ltd.), and "SILICONE FZ-2233" (HLB: 2, viscosity: 5,000 mm$^2$/s, Dow Corning Toray Co., Ltd.).

These polyether-modified silicones can be used either singly or in combination. The polyether-modified silicone may be contained at preferably from 0.1 to 6 wt. %, more preferably from 0.3 to 2.4 wt. % in the whole composition, because the cosmetic is sufficient in the fixing property of makeup and is excellent in long-lasting property.

The weight ratio of the component (A) to the component (D), (A)/(D), may be preferably from 1.2 to 30, more preferably from 1.4 to 25, even more preferably from 2.3 to 12.5.

This range can facilitate the fixing of a makeup, can perform an even application, and can obtain a smooth finish.

In the present invention, (E) flaky powder of zinc oxide having an average particle size of from 0.1 to 6 μm, an average particle thickness of from 0.01 to 0.3 μm and an average plate ratio of 3 or greater may be further contained as a powder. The resulting cosmetic can also provide a feel of transparency and a moist feel while retaining excellent covering power.

Such flaky powder of zinc oxide may have an average particle size of from 0.1 to 6 μm, with from 0.1 to 1 μm being preferred and from 0.2 to 0.8 μm being more preferred. An average particle size of smaller than 0.1 μm causes aggregation so that the dispersibility is lowered. An average particle size of greater than 6 μm, on the other hand, leads to reductions in transparency and ultraviolet absorptivity. The average particle thickness may be from 0.01 to 0.3 μm, preferably from 0.015 to 0.2 μm, more preferably from 0.02 to 0.1 μm. An average particle thickness of smaller than 0.01 μm tends to cause crumbling of the flake form, while an average particle thickness of greater than 0.3 μm may give a feel of discomfort when added in a cosmetic. In addition, the average plate ratio may be 3 or greater, with 5 or greater being more preferred and 10 or greater being even more preferred. Although no upper limit is specifically imposed on the plate ratio, one having an average plate ratio of from 50 or smaller, preferably from 30 or smaller is generally used. A plate ratio of smaller than 3 tends to result in reduced transparency.

In the present invention, each average particle size is determined as the arithmetic average of major and minor axes from an electron micrograph, and its corresponding plate ratio is determined as an average particle size/average particle thickness by similarly reading plate thicknesses from the electron micrograph.

Although the flaky powder of zinc oxide as the component (E) may consist of zinc oxide alone, it may contain a small amount of another element, in other words, it may be doped. As such doping elements, iron, zirconium, calcium, manganese, magnesium, yttrium and the like can be mentioned, and these doping elements can be used either singly or in combination. Iron is preferred as a doping element. The doping level may preferably be, but is not limited to, from 0.005 to 1 mole %, with from 0.01 to 0.5 mol % being more preferred, based on the zinc. In this range, flaky powder of zinc oxide particles having a highplate ratio and an excellent feel of transparency can be obtained. Its combined use with the component (A), i.e., the vinyl-based polymer having the carbosiloxane dendrimer structure in a side chain thereof makes it possible to provide high covering power.

The flaky powder of zinc oxide as the component (E) can be produced, for example, according to the procedure described in JP-A-7-330334.

As the component (E), one or more flaky powder of zinc oxides can be used. The component (E) may be contained at preferably from 0.1 to 20 wt. %, more preferably from 0.5 to 8 wt. % in the whole composition, because no tight feel is given and a sufficient moist feel can be obtained.

In the present invention, the weight ratio of the component (A) to the component (E), (A)/(E), may be preferably from 0.05 to 20, more preferably from 0.1 to 10, even more preferably from 0.25 to 4. When the (A)/(E) falls within this range, extremely high moist feel and covering power can be obtained.

The cosmetic according to the present invention may further contain, as a component (F), (F1) a poly(N-acylalkyleneimine)-modified silicone and/or (F2) a sugar-modified silicone, so that a finish with an adhesion feel can be obtained.

The poly(N-acylalkyleneimine)-modified silicone useful as the component (F1) in the present invention is a copolymer having organopolysiloxane segments and poly(N-acylalkyleneimine), and takes a viscous liquid form, rubbery form or solid form at room temperature and under a normal pressure because it forms intermolecular crosslinks by bonding other than covalent bonding.

Preferred as the poly(N-acylalkyleneimine)-modified silicone is, for example, one containing segments of a poly(N-acylalkyleneimine), which is formed of repeating units represented by the following formula (3):

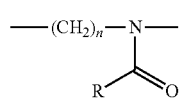
(3)

wherein R represents a hydrogen atom, an alkyl group having from 1 to 12 carbon atoms, a cycloalkyl group, an aralkyl group or an aryl group, and n is 2 or 3, and segments of an organopolysiloxane in a molecule thereof, in which to at least one of end or side-chain silicon atoms in each of the segments of the organopolysiloxane, one of the segments of the poly (N-acylalkyleneimine) formed of the repeating units represented by the formula (3) is bonded via an alkylene group containing a hetero atom. The weight ratio of the segments of the poly(N-acylalkyleneimine) to the segments of the organopolysiloxane may be preferably from 1/50 to 20/1, more preferably from 1/40 to 2/1, and the molecular weight of the poly(N-acylalkyleneimine)-modified silicone may be from 500 to 500,000, more preferably from 1,000 to 300,000. Further, R may preferably be a methyl or ethyl group.

The alkylene group, which contains the hetero atom and is bonded to at least one of the end or side-group silicon atoms in each segment of the organopolysiloxane, can be an alkylene group having from 2 to 20 carbon atoms and containing from 1 to 3 nitrogen atoms, oxygen atoms or sulfur atoms, with a nitrogen-containing alkylene group having from 2 to 5 carbon atoms being preferred.

Preferred examples of the poly(N-acylalkyleneimine)-modified silicone include poly(N-formylethyleneimine)-modified silicone, poly(N-acetylethyleneimine)-modified silicone, and poly(N-propionylethyleneimine)-modified silicone. Of these, more preferred is a poly(N-propionylethyleneimine)-modified silicone having a weight average molecular weight of from about 20,000 to 200,000 and containing poly(N-propionylethyleneimine) segments in a proportion of from about 3 to 50 wt. % in the molecule (INCI name: polysilicone-9: "ELASTOMER OS", Kao Corporation).

The poly(N-acylalkyleneimine)-modified silicone can be produced by a known procedure, for example, the procedure described in JP-A-7-133352.

The molecular weight of the molecular chain of the poly (N-acylalkyleneimine) may be preferably from 150 to 50,000, more preferably from 500 to 10,000 from the viewpoints of the stability and feel upon use of the cosmetic. The setting of the molecular weight at 150 or higher can provide excellent stability, while the setting of the molecular weight at 50,000 or lower can provide a good feel upon use.

In the present invention, the sugar-modified silicone useful as the component (F2) contains a sugar-derived residual group in one end or both ends or one or more side chains of the molecular chain.

In this sugar-modified silicone (F2), the sugar-derived residual group can be a sugar-lactone amidoalkyl group (a group of a sugar lactone compound and an aminoalkyl group bonded together through an amide linkage). Preferred as the sugar-modified silicone is one containing silicone chains at from 40 to 97 wt. %, desirably from 50 to 85 wt. % and having a weight average molecular weight of from 5,000 to 500,000, desirably from 50,000 to 300,000. A greater extent of modification with sugar-derived residual groups tends to result in better stability, while a smaller extent of modification with sugar-derived residual groups tends to lead to a better feel upon use. On the other hand, a higher molecular weight tends to result in better stability, while a lower molecular weight tends to show excellent spreading.

The sugar-modified silicone (F2) can be produced, for example, by reacting a sugar lactone compound (one obtained by intramolecularly cyclodehydrating aldonic acid or uronic acid) to an organopolysiloxane having at least one aminoalkyl group such that amide linkages are formed.

The aminoalkyl group may preferably be an aminoalkyl group having from 1 to 20 carbon atoms, with an aminoalkyl group having from 1 to 8 carbon atoms being more preferred. Examples of the lactone compound, which is obtained by subjecting aldonic acid or uronic acid to intramolecular cyclization, include aldonic acid lactones derived from reducing monosaccharides such as D-glucose, D-galactose, D-allose, D-altrose, D-mannose, D-gulose, D-idose and D-talose; aldonic acid lactones derived from reducing disaccharides such as maltose, cellobiose, lactose, xylobiose, isomaltose, nigerose and kojibiose; aldonic acid lactones derived from reducing trisaccharides such as maltotriose, panose and isomaltotriose; aldonic acid lactones derived from reducing, tetra and higher oligosaccharides; and uronic acid lactones such as D-glucuronic acid, L-iduronic acid and mannuronic acid. These lactone compounds can be subjected either singly or in combination to the reaction.

The reaction between the organopolysiloxane precursor having one or more aminoalkyl groups and the sugar lactone can be performed preferably by using the sugar lactone in an amount of 1.0 to 1.3 mol times per 1 mol of the one or more amino groups in the organopolysiloxane precursor, mixing them in a solvent, and stirring at a solution concentration of 5 to 30 wt. % for 3 to 20 hours under heating and reflux. As the solvent for use in the above-described reaction, a lower alcohol such as methanol, ethanol, 1-propanol or 2-propanol is preferred.

The sugar-modified silicone for use in the present invention may also contain other functional groups to extent that its properties are not impaired.

Specific examples of the sugar-modified silicone useful as the component (F2) in the cosmetic composition according to the present invention include, for example, those of Synthesis Examples 8 to 10 and Comparative Synthesis Example 3 described in JP-A-7-133352. In addition, commercial products, for example, a silicone having a gluconamido group at both ends (one having from 300 to 350 repeating silicone units; "DOW CORNING CE-8810 SUGAR SILICONE EMULSION", product of Dow Corning Toray Co., Ltd.) can also be used suitably.

As the component (F), one or more of such modified silicones can be used and the components (F1) and (F2) can be also used in combination. The content of the component (F) may be preferably from 0.1 to 30 wt. %, more preferably from 0.1 to 20 wt. % from the viewpoint of stability. The content of 0.1 wt. % or higher can result in high water repellency, while the content of 30 wt. % or lower can result in good spreading upon use.

The weight ratio of the component (A) to the component (F), (A)/(F), may be preferably in the range of from 0.003 to 300, more preferably in the range of from 0.005 to 200 from the viewpoints of suppression of over-shinning and a finish with an adhesion feel. The setting of the weight ratio (A)/(F) at 0.003 or greater can give a finish with an adhesion feel while avoiding over-shinning, and the setting of the weight ratio (A)/(F) at 300 or smaller can exhibit excellent stability.

The cosmetic according to the present invention may further contain (G) a volatile solvent. The volatile solvent has a normal pressure boiling point of from 70 to 250° C., and therefore, is liquid at room temperature. Specific examples include linear siloxanes such as polydimethylsiloxane (1.5 cs) and polydimethylsiloxane (2 cs); branched siloxanes such as tris(trimethylsilyl)methylsilane and tetrakis(trimethylsilyl)silane; cyclic siloxanes such as decamethylcyclopentasiloxane and dodecamethylcyclohexasiloxane; and hydrocarbon oils such as isododecane and light liquid paraffin.

The content of the volatile solvent may be preferably from 0.1 to 90 wt. %, more preferably from 0.5 to 60 wt. % from the viewpoint of a feel of use upon application. Within this range, spreading and compatibility are good. This range is, therefore, preferred.

It is to be noted that a volatile solvent, which is employed to dissolve or disperse the component (A), i.e., the vinyl-based copolymer having the carbosiloxane dendrimer structure in a side chain thereof, is included in the component (G).

The cosmetic according to the present invention can be formulated into various product forms. Such product forms include milk lotions, creams, pastes and gel preparations in water-in-oil, oil-in-water or multi-emulsion forms; powder preparations; oil preparations; oil-based solid preparations; and the like. More preferred product forms are water-in-oil product forms.

When desired to formulate into a water-in-oil emulsified cosmetic, its viscosity at 25° C. may be preferably from 500 to 200,000 Pa·s, more preferably from 1,000 to 100,000 Pa·s, even more preferably from 2,000 to 50,000 Pa·s because such a viscosity can provide excellent covering power. It is to be noted that this viscosity is a value measured by a Brookfield viscometer.

When desired to formulate into a water-in-oil emulsified cosmetic, a nonionic surfactant and water are contained.

As the nonionic surfactant, the component (D), i.e., the polyether-modified silicone can be suitably used. As an alternative, one employed in ordinary cosmetics can also be used. No limitation is imposed on the HLB of the nonionic surfactant, but a hydrophobic surfactant having the HLB of from 1 to 7 is preferred. Examples include dimethylpolysiloxane-monoalkyl glyceryl ether copolymers, silicone-based surfactants other than polyether-modified silicones such as polyglycerin-modified silicone, glycerin fatty acid esters, polyoxyethylene glycerin fatty acid esters, polyglycerin fatty acid esters, propylene glycol fatty acid esters, sorbitan fatty acid esters, polyoxyethylene sorbit/sorbitan fatty acid esters, polyoxyethylene castor oil, polyoxyethylene hydrogenated castor oil, ethylene glycol fatty acid esters, polyethylene glycol fatty acid esters, alkyl glyceryl ethers, polyoxyethylene alkyl ethers, and polyoxyethylene alkyl ether fatty acid esters.

As the nonionic surfactant, a dimethylpolysiloxane-polyoxyalkylene copolymer or a dimethylpolysiloxane-monoalkylglyceryl ether copolymer is preferred, with one having an HLB of from 1 to 6 being more preferred from the standpoints of the long-lasting property of makeup and stability.

One or more of such nonionic surfactants can be used. The nonionic surfactant may be contained at preferably from 0.1 to 6 wt. %, more preferably from 0.3 to 3.5 wt. % in the whole composition from the standpoints of the stability of the emulsified product and the long-lasting property of makeup.

On the other hand, water may be contained at preferably from 0.1 to 90 wt. %, more preferably from 10 to 60 wt. % in the whole composition.

The cosmetic according to the present invention can contain, in addition to the above-described components, components commonly employed in cosmetic compositions, for example, oily substances other than those described above, pigments, water-soluble polymers, antioxidants, fragrances, colorants, preservatives, ultraviolet light absorbers, thickening agents, pH regulators, blood circulation promoters, cooling agents, antiperspirants, bactericides, skin activators, humectants, algefacients, and the like within qualitative and quantitative ranges not impairing the object and advantageous effects of the present invention.

When an oily substance other than the above-described ones is used as the additional components, one having a solubility parameter of 12 or less is preferred. Usable examples include liquid paraffin; and fluorine-containing cosmetic oils and fluorine-modified silicone oils, such as silicone oil, perfluoropolyether, perfluorodecaline and perfluorooctane.

Among these optional components, the lower alcohol such as methanol, ethanol, propanol or isopropanol may be used at preferably 10 wt. % or lower, more preferably 7 wt. % or lower from the standpoints of a feel upon use and stability.

The cosmetic composition according to the present invention can be produced by a usual procedure.

When formulating a water-in-oil emulsified cosmetic, it can be produced by mixing oil-phase components, adding powder components thereto, further adding water-phase components to the mixture, and then conducting stirring and mixing. No limitation is imposed on the mixing method, and usual high-speed agitation equipment such as a vacuum emulsifying mixer or homomixer can be used.

The cosmetic composition according to the present invention can be applied as a skin care cosmetic composition such as a liquid-type milk lotion, cream or cleansing product; a makeup cosmetic such as a foundation, make up base, cheek color, eye shadow, mascara, eyeliner, eyebrow cosmetic, overcoat or lipstick; or the like.

EXAMPLES

Examples 1-7 and Comparative Examples 1-9

Water-in-oil emulsified foundations of the composition shown in Table 1 and Table 2 were produced, and were then evaluated for a feel upon use (spreadability, stickiness, film feeling), a finish feel (concealment of pores), the long-lasting property of makeup, the concealment of pores after 5 hours, and the concealment of creases. The results are shown together in Table 1 and Table 2.

(Procedure)

The oil-phase components and polymer components were uniformly mixed, followed by dispersing the powder components in the oil-phase components by a vacuum emulsifying mixer, and then gradually adding a mixture of the water-phase components into the dispersion while stirring, whereby the resultant mixture was emulsified. Thus, each target two-layer separation water-in-oil emulsified foundation was obtained.

(Evaluation Methods)

(1) Feel Upon Use (Spreadability)

By 10 expert evaluators, a sensory evaluation of spreadability was performed when each water-in-oil emulsified cosmetic was used. The evaluation results were ranked in accordance with the following standards.

A⁺: Evaluated "good" by 8 or more expert evaluators.
A: Evaluated "good" by 6 or 7 expert evaluators.
B: Evaluated "good" by 4 or 5 expert evaluators.
C: Evaluated "good" by 3 or fewer expert evaluators.

(2) Feel Upon Use (Stickiness)

By the 10 expert evaluators, a sensory evaluation of stickiness was performed when each water-in-oil emulsified cosmetic was used. The evaluation results were ranked in accordance with the following standards.

A⁺: Evaluated "low" by 8 or more expert evaluators.
A: Evaluated "low" by 6 or 7 expert evaluators.
B: Evaluated "low" by 4 or 5 expert evaluators.
C: Evaluated "low" by 3 or fewer expert evaluators.

(3) Film Feeling (Tightness, Pressure Feel, Discomfort)

By the 10 expert evaluators, a sensory evaluation of the absence of tightness, pressure feel or discomfort was performed when each water-in-oil emulsified cosmetic was used. The evaluation results were ranked in accordance with the following standards.

A⁺: Evaluated "low" by 8 or more expert evaluators.
A: Evaluated "low" by 6 or 7 expert evaluators.
B: Evaluated "low" by 4 or 5 expert evaluators.
C: Evaluated "low" by 3 or fewer expert evaluators.

(4) Finish Feel (Concealment of Pores)

By the 10 expert evaluators, a sensory evaluation of the concealment of pores was performed when each water-in-oil emulsified cosmetic was used. The evaluation results were ranked in accordance with the following standards.

A⁺: Evaluated "hardly visible" by 8 or more expert evaluators.
A: Evaluated "hardly visible" by 6 or 7 expert evaluators.
B: Evaluated "hardly visible" by 4 or 5 expert evaluators.
C: Evaluated "hardly visible" by 3 or fewer expert evaluators.

(5) Long-Lasting Property of Makeup

By the 10 expert evaluators, a sensory evaluation of the long-lasting property of makeup was performed when each water-in-oil emulsified cosmetic was used. The evaluation results were ranked in accordance with the following standards.

A⁺: Evaluated "good" by 8 or more expert evaluators.
A: Evaluated "good" by 6 or 7 expert evaluators.
B: Evaluated "good" by 4 or 5 expert evaluators.
C: Evaluated "good" by 3 or fewer expert evaluators.

(6) Concealment of Creases after 5 Hours

By the 10 expert evaluators, a sensory evaluation of the concealment of creases after 5 hours was performed when each water-in-oil emulsified cosmetic was used. The evaluation results were ranked in accordance with the following standards.

A⁺: Evaluated "hardly visible" by 8 or more expert evaluators.
A: Evaluated "hardly visible" by 6 or 7 expert evaluators.
B: Evaluated "hardly visible" by 4 or 5 expert evaluators.
C: Evaluated "hardly visible" by 3 or fewer expert evaluators.

(7) Concealment of Pores after 5 Hours

By the 10 expert evaluators, a sensory evaluation of the concealment of pores after 5 hours was performed when each water-in-oil emulsified cosmetic was used. The evaluation results were ranked in accordance with the following standards.

A⁺: Evaluated "hardly visible" by 8 or more expert evaluators.
A: Evaluated "hardly visible" by 6 or 7 expert evaluators.
B: Evaluated "hardly visible" by 4 or 5 expert evaluators.
C: Evaluated "hardly visible" by 3 or fewer expert evaluators.

TABLE 1

| Components (wt. %) | Examples | | | | | | |
|---|---|---|---|---|---|---|---|
| | 1 | 2 | 3 | 4 | 5 | 6 | 7 |
| Silicone dendrimer-acrylate copolymer[*1] | 5.0 | 15.0 | 20.0 | 15.0 | 15.0 | 15.0 | 15.0 |
| Dimethylpolysiloxane-polyoxyethylene copolymer[*2] | 0.5 | 0.5 | 0.5 | 0.5 | 0.5 | 0.5 | 0.5 |
| Decamethylcyclopentasiloxane | 10.0 | 5.0 | | 4.0 | 4.0 | 5.0 | 5.0 |
| Dimethylpolysiloxane (2 cs) | 10.0 | 10.0 | 10.0 | 10.0 | 10.0 | 10.0 | 10.0 |
| Dimethylpolysiloxane (6 cs) | 6.0 | 6.0 | 6.0 | 6.0 | 6.0 | 6.0 | 6.0 |
| 2-Ethylhexyl paramethoxycinnamate[*3] | 3.0 | 3.0 | 3.0 | | 1.5 | 1.5 | 1.5 |
| Diisostearyl malate[*4] | | | | | | | 1.5 |
| Glyceryl tri(2-ethylhexanoate)[*5] | | | | | 1.5 | | |
| Neopentyl glycol dicaprate[*6] | | | | 3.0 | | 1.5 | |
| Glycerin | 2.0 | 2.0 | 2.0 | 2.0 | 2.0 | 2.0 | 2.0 |
| Ethanol | 7.0 | 7.0 | 7.0 | 7.0 | 7.0 | 7.0 | 7.0 |
| Magnesium sulfate | 0.5 | 0.5 | 0.5 | 0.5 | 0.5 | 0.5 | 0.5 |
| Purified water | Balance | Balance | Balance | Balance | Balance | Balance | Balance |
| Silicone-treated fine particulate zinc oxide[*7] | 2.0 | 2.0 | 2.0 | 2.0 | 2.0 | 2.0 | 2.0 |
| Silicone-treated fine particulate titanium dioxide ("MT600B", Tayka Corporation)[*8] | 1.5 | 1.5 | 1.5 | 1.5 | 1.5 | 1.5 | 1.5 |
| Silicone-treated titanium dioxide[*8] | 6.0 | 6.0 | 6.0 | 6.0 | 6.0 | 6.0 | 6.0 |
| Silicone-treated iron oxide (red, yellow, black)[*8] | 1.8 | 1.8 | 1.8 | 1.8 | 1.8 | 1.8 | 1.8 |
| Silicone-treated titanium dioxide-coated mica (violet interference light system)[*8] ("FLAMENCO SATIN VIOLET", BASF SE, average particle size: 8 μm) | 1.5 | 1.5 | 1.5 | 1.5 | 1.5 | 1.5 | 1.5 |
| Silsesquioxane[*9] | 2.5 | 2.5 | 2.5 | 2.5 | 2.5 | 2.5 | 2.5 |
| Total | 100 | 100 | 100 | 100 | 100 | 100 | 100 |
| (A)/(B) weight ratio | 0.5 | 1.5 | 2.0 | 1.5 | 1.5 | 1.5 | 1.5 |

TABLE 1-continued

|  | Examples | | | | | | |
|---|---|---|---|---|---|---|---|
| Components (wt. %) | 1 | 2 | 3 | 4 | 5 | 6 | 7 |
| Feel upon use: | | | | | | | |
| Spreadability | A+ | A | A | A+ | A | A+ | A+ |
| Stickiness | A+ | A+ | A | A | A+ | A+ | A+ |
| Film feeling | A+ | A | A | A | A+ | A+ | A |
| Finish feel (concealment of pores) | A | A+ | A+ | A+ | A+ | A+ | A+ |
| Long-lasting property of makeup | A | A+ | A | A | A+ | A+ | A |
| Concealment of pores after 5 hrs. | A | A+ | A+ | A | A+ | A+ | A+ |
| Concealment of creases after 5 hrs. | A | A+ | A | A | A+ | A+ | A |

*[1]"FA4001CM" (Dow Corning Toray Co., Ltd); 30% decamethylcyclopentasiloxane solution
*[2]"SH3775M" (Dow Corning Toray Co., Ltd.); HLB: 5
*[3]"PARSOL MCX" (DSM Nutrition Japan K.K.); SP value: 19.2
*[4]"COSMOL 222" (The Nisshin Oilio Group, Ltd.); SP value: 17.9
*[5]"EXCEPARL TGO" (Kao Corporation); SP value: 18.6
*[6]"ESTEMOL N-01" (The Nisshin Oilio Group, Ltd.); SP value: 18.2
*[7]"MZ504R3M" (Tayka Corporation): 0.02 μm
*[8]Treated at 2 wt. % with methylhydrogenpolysiloxane
*[9]"TOSPARL 145" (Dow Corning Toray Co., Ltd.)

TABLE 2

|  | Comparative Examples | | | | | | | | |
|---|---|---|---|---|---|---|---|---|---|
| Components (wt. %) | 1 | 2 | 3 | 4 | 5 | 6 | 7 | 8 | 9 |
| Silicone dendrimer-acrylate copolymer*[1] | 1.0 | 15.0 | 3.0 | 9.0 | 20.0 | 9.0 | | | |
| Acrylate-silicone copolymer*[10] | | | | | | | 9.0 | 9.0 | |
| Trimethylsiloxysilicate*[11] | | | | | | | | | 9.0 |
| Dimethylpolysiloxane-polyoxyethylene copolymer*[2] | 0.5 | 0.5 | 0.5 | 0.5 | 0.5 | 0.5 | 0.5 | 0.5 | 0.5 |
| 2-Ethylhexyl paramethoxycinnamate*[3] | 3.0 | 0.5 | | | | | | 3.0 | 3.0 |
| Decamethylcyclopentasiloxane | 15.0 | 15.0 | 15.0 | 15.0 | 15.0 | 15.0 | 15.0 | 15.0 | 15.0 |
| Dimethylpolysiloxane (2 cs) | 10.0 | 10.0 | 10.0 | 10.0 | 10.0 | 10.0 | 10.0 | 10.0 | 10.0 |
| Dimethylpolysiloxane (6 cs) | 6.0 | 6.0 | 6.0 | 6.0 | 6.0 | 6.0 | 6.0 | 6.0 | 6.0 |
| Squalane (SP value: 16.3) | | | | | | 3.0 | | | |
| Glycerin | 2.0 | 2.0 | 2.0 | 2.0 | 2.0 | 2.0 | 2.0 | 2.0 | 2.0 |
| Ethanol | 7.0 | 7.0 | 7.0 | 7.0 | 7.0 | 7.0 | 7.0 | 7.0 | 7.0 |
| Magnesium sulfate | 0.5 | 0.5 | 0.5 | 0.5 | 0.5 | 0.5 | 0.5 | 0.5 | 0.5 |
| Purified water | Balance | Balance | Balance | Balance | Balance | Balance | Balance | Balance | Balance |
| Silicone-treated fine particulate zinc oxide*[7] | 2.0 | 2.0 | 2.0 | 2.0 | 2.0 | 2.0 | 2.0 | 2.0 | 2.0 |
| Silicone-treated fine particulate titanium dioxide ("MT600B", Tayka Corporation)*[8] | 1.5 | 1.5 | 1.5 | 1.5 | 1.5 | 1.5 | 1.5 | 1.5 | 1.5 |
| Silicone-treated titanium dioxide*[8] | 6.0 | 6.0 | 6.0 | 6.0 | 6.0 | 6.0 | 6.0 | 6.0 | 6.0 |
| Silicone-treated iron oxide (red, yellow, black)*[8] | 1.8 | 1.8 | 1.8 | 1.8 | 1.8 | 1.8 | 1.8 | 1.8 | 1.8 |
| Silicone-treated titanium dioxide coated mica (violet interference light system)*[8] ("FLAMENCO SATIN VIOLET", BASF SE, average particle size: 8 μm) | 1.5 | 1.5 | 1.5 | 1.5 | 1.5 | 1.5 | 1.5 | 1.5 | 1.5 |
| Silsesquioxane*[9] | 2.5 | 2.5 | 2.5 | 2.5 | 2.5 | 2.5 | 2.5 | 2.5 | 2.5 |
| Total | 100 | 100 | 100 | 100 | 100 | 100 | 100 | 100 | 100 |
| (A)/(B) weight ratio | 0.1 | 9.0 | — | — | — | — | — | — | — |
| Feel upon use: | | | | | | | | | |
| Spreadability | A | A | A | B | C | A | A | A | A |
| Stickiness | B | B | A | B | C | B | A | B | B |
| Film feeling | A | C | B | B | C | B | B | B | B |
| Finish feel (concealment of pores) | B | A | B | B | B | B | B | B | B |
| Long-lasting property of makeup | C | B | C | B | A | C | B | B | C |

TABLE 2-continued

| | Comparative Examples | | | | | | | | |
|---|---|---|---|---|---|---|---|---|---|
| Components (wt. %) | 1 | 2 | 3 | 4 | 5 | 6 | 7 | 8 | 9 |
| Concealment of pores after 5 hrs | C | C | C | C | B | C | C | C | C |
| Concealment of creases after 5 hrs | C | C | C | C | B | C | B | C | C |

*[1]"FA4001CM" (Dow Corning Toray Co., Ltd); 30% decamethylcyclopentasiloxane solution
*[2]"SH3775M" (Dow Corning Toray Co., Ltd.)
*[3]"PARSOL MCX" (DSM Nutrition Japan K.K.); SP value: 19.2
*[7]"MZ504R3M" (Tayka Corporation): 0.02 μm
*[8]Treated at 2 wt. % with methylhydrogenpolysiloxane
*[9]"TOSPARL 145" (Dow Corning Toray Co., Ltd.)
*[10]"KP-545" (Shin-Etsu Chemical Co., Ltd.); 30% decamethylcyclopentasiloxane solution
*[11]"KF-7312J" (Shin-Etsu Chemical Co., Ltd.); 50% decamethylcyclopentasiloxane solution

Example 8

Make Up Base ((A)/(B)=0.8)

(Components)

| | | |
|---|---|---|
| (1) | Dimethylpolysiloxane-polyoxyethylene copolymer ("KF6015", Shin-Etsu Chemical Co., Ltd.) | 2 (wt. %) |
| (2) | Silicone dendrimer-acrylate copolymer ("FA4002ID", 40% isododecane solution, product of Dow Corning Toray Co., Ltd.) | 6 |
| (3) | Decamethylcyclopentasiloxane | 20 |
| (4) | Perfluoropolyether ("FOMBLIN HC/R", Solvay Solexis S.A.) | 3 |
| (5) | Neopentyl glycol dicaprate ("ESTEMOL N-01", The Nisshin Oilio Group, Ltd.; SP value: 18.2) | 3 |
| (6) | Fluorine compound-treated pigment (treated at 5% with perfluoroalkylphosphate ester) Red-iron-oxide-coated titanated mica ("FLAMENCO SATIN VIOLET", product of BASF SE) | 1.5 |
| (7) | Silicone-treated pigments | |
| | Titanium dioxide | 0.6 |
| | Iron oxide (red, yellow, black) | 0.2 |
| (8) | Paraben | 0.1 |
| (9) | Ethanol | 1 |
| (10) | Glycerin | 5 |
| (11) | Purified water | Balance |
| | Total | 100 |

(Procedure)

The components (1) to (5) were mixed. To the mixture, the components (6) and (7) were added, followed by dispersion in a vacuum emulsifying mixer. While stirring the resultant mixture, a mixture of the components (8) to (10) was gradually added dropwise. After emulsification was conducted further in a homomixer, the emulsion was defoamed to obtain a make up base.

Example 9

Creamy Foundation ((A)/(B)=0.7)

(Components)

| | | |
|---|---|---|
| (1) | Glyceryl-ether-modified silicone (Compound (L) described in Example 11 of JP-A-4-108795) | 3 (wt. %) |
| (2) | Silicone dendrimer-acrylate copolymer ("FA4002ID", 40% isododecane solution, product of Dow Corning Toray Co., Ltd.) | 10 |
| (3) | Polydimethylsiloxane (1.5 cs) | 12 |
| (4) | Fluorine-modified silicone (Compound described in Example 4 of JP-A-6-184312) | 4 |
| (5) | Neopentyl glycol dicaprate ("ESTEMOL N-01", The Nisshin Oilio Group, Ltd.; SP value: 18.2) | 2 |
| (6) | Methylphenylpolysiloxane ("KF-53", Shin-Etsu Chemical Co., Ltd.; SP value: 20.0) | 1 |
| (7) | 2-Ethylhexyl paramethoxycinnamate ("PARSOL MCX, DSM Nutrition Japan K.K.; SP value: 19.2) | 3 |
| (8) | Fluorine compound-treated pigment (treated at 5% with perfluoroalkylphosphate ester) Red-iron-oxide-coated titanated mica ("FLAMENCO SATIN VIOLET", product of BASF SE) | 1.5 |
| | Titanium dioxide | 6 |
| | Iron oxide (red, yellow, black) | 4 |
| (9) | Paraben | 0.1 |
| (10) | Ethanol | 1.0 |
| (11) | Glycerin | 5 |
| (12) | Purified water | Balance |
| | Total | 100 |

(Procedure)

The components (1) to (6) were mixed. To the mixture, the component (7) was added, followed by dispersion in a vacuum emulsifying mixer. While stirring the resultant mixture, a mixture of the components (8) to (10) was gradually added dropwise. After emulsification was conducted further in a homomixer, the emulsion was defoamed to obtain a creamy foundation.

Example 10

Sunscreen Cosmetic ((A)/(B)=1.0)

(Components)

| | | |
|---|---|---|
| (1) | Polydimethylsiloxane (1.5 cs) | 15 (wt. %) |
| (2) | Silicone dendrimer-acrylate copolymer ("FA4002ID", 40% isododecane solution, product of Dow Corning Toray Co., Ltd.) | 15 |
| (3) | Dimethylpolysiloxane-polyoxyethylene copolymer ("SH3775M", Shin-Etsu Chemical Co., Ltd.) | 1.5 |
| (4) | Polydimethylsiloxane (6 cs) | 3 |

-continued

| | | |
|---|---|---|
| (5) | 2-Ethylhexyl paramethoxycinnamate ("PARSOL MCX, DSM Nutrition Japan K.K.; SP value: 19.2) | 3 |
| (6) | Silicone-treated fine particulate titanium dioxide (Obtained by treating "MT-600B" (Tayka Corporation) at 2% with methylhydrogenpolysiloxane) | 3 |
| (7) | Spherical nylon powder ("SP-500", product of Toray Industries, Inc.) | 1.5 |
| (8) | Ethanol | 3 |
| (9) | Trisethoxydiglycol phosphate (SP value: 18.1) | 3 |
| (10) | Paraben | 0.1 |
| (11) | Purified water | Balance |
| | Total | 100 |

(Procedure)

The components (1) to (5) were mixed. To the mixture, the components (6) and (7) were added, followed by dispersion in a vacuum emulsifying mixer. While stirring the resultant mixture, a mixture of the components (8) to (11) was gradually added dropwise. After emulsification was conducted further in a homomixer, the emulsion was defoamed to obtain a sunscreen cosmetic.

Example 11

Control Color ((A)/(B)=2.0)

(Components)

| | | |
|---|---|---|
| (1) | Dimethylpolysiloxane-polyoxyethylene copolymer ("KF6015", Shin-Etsu Chemical Co., Ltd.) | 2 (wt. %) |
| (2) | Silicone dendrimer-acrylate copolymer ("FA4001CM", 30% decamethylcyclopentasiloxane solution, product of Dow Corning Toray Co., Ltd.) | 6 |
| (3) | Decamethylcyclopentasiloxane | 20 |
| (4) | Polydimethylsiloxane (6 cs) | 3 |
| (5) | Neopentyl glycol dicaprate ("ESTEMOL N-01", The Nisshin Oilio Group, Ltd.; SP value: 18.2) | 0.9 |
| (6) | Fluorine compound-treated red-iron-oxide-coated titanated mica ("FLAMENCO SATIN GREEN", product of BASF SE) (treated at 5 wt. % with perfluoroalkyl ethylphosphate diethanolamine) | 5 |
| (7) | Paraben | 0.1 |
| (8) | Ethanol | 1 |
| (9) | Glycerin | 2 |
| (10) | Purified water | Balance |
| | Total | 100 |

(Procedure)

The components (1) to (5) were mixed. To the mixture, the component (6) was added, followed by dispersion in a vacuum emulsifying mixer. While stirring the resultant mixture, a mixture of the components (7) to (10) was gradually added dropwise. After emulsification was conducted further in a homomixer, the emulsion was defoamed to obtain a control color.

Example 12

Creamy Concealer ((A)/(B)=2.0)

(Components)

| | | |
|---|---|---|
| (1) | Dimethylpolysiloxane-polyoxyethylene copolymer ("KF6015", Shin-Etsu Chemical Co., Ltd.) | 3.5 (wt. %) |
| (2) | Silicone dendrimer-acrylate copolymer ("FA4002ID", 40% isododecane solution, product of Dow Corning Toray Co., Ltd.) | 20 |
| (3) | Isododecane | 10 |
| (4) | Polydimethylsiloxane (6 cs) | 2 |
| (5) | Polyglyceryl-2 triisostearate ("COSMOL 43" (The Nisshin Oilio Group, Ltd.); SP value: 18.7) | 1 |
| (6) | Diisostearyl malate ("COSMOL 222" (The Nisshin Oilio Group, Ltd.); SP value: 16.7) | 3 |
| (7) | Tocopherol ("TOCOPHEROL 80" (The Nisshin Oilio Group, Ltd.); SP value: 19.4) | 0.1 |
| (8) | Silicone-treated pigments | |
| | Titanium dioxide | 6 |
| | Iron oxide (red, yellow, black) | 1.5 |
| | Titanated mica ("TIMIRON SUPER GOLD", Merck & Co., Inc.) | 0.5 |
| | Titanated mica ("PRESTIGE BRIGHT GOLD", ECKART GmbH) | 0.1 |
| (9) | Paraben | 0.1 |
| (10) | Ethanol | 1 |
| (11) | Purified water | Balance |
| | Total | 100 |

(Procedure)

The components (1) to (7) were mixed. To the mixture, the component (8) was added, followed by dispersion in a vacuum emulsifying mixer. While stirring the resultant mixture, a mixture of the components (9) to (11) was gradually added dropwise. After emulsification was conducted further in a homomixer, the emulsion was defoamed to obtain a creamy concealer.

The water-in-oil emulsified cosmetics obtained in Examples 9 to 12 were each good in a feel upon use, were each able to form an even cosmetic film on the skin, were each low in film feeling after applied to the skin, and were each excellent in skin adhesion and also in the effects that make fine wrinkles and pores hardly visible. Further, they were each good in the long-lasting property of makeup, and were each able to keep pores and creases hardly visible with time.

Examples 13-23 and Comparative Examples 10-13

Water-in-oil emulsified foundations of the formulations shown in Table 3 and Table 4 were produced, and in the similar evaluation method as the foregoing, were then evaluated for the concealment of pores shortly after application, the concealment of skin pores 5 hours after application, the concealment of creases 5 hours after application, and were also evaluated for a feel upon use (film feeling) and the ease of makeup fixing. The results are shown together in Table 3 and Table 4.

(Procedure)

The oil-phase components and polymer components were uniformly mixed, followed by dispersing the powder components in the oil-phase components by a vacuum emulsifying mixer, and then gradually adding a mixture of the water-phase components into the dispersion while stirring, whereby the resultant mixture was emulsified. Thus, each target water-in-oil emulsified foundation was obtained.

(Evaluation Methods)

(1) Feel Upon Use (Film Feeling (Tightness, Feeling of Pressure, Discomfort))

By the 10 expert evaluators, a sensory evaluation of the existence or non-existence of a film feeling (tightness, feeling of pressure, discomfort) was performed when each water-in-oil emulsified cosmetic was used. The evaluation results were ranked in accordance with the following standards.

A+: Evaluated "low" in film feeling by 8 or more expert evaluators.
A: Evaluated "low" in film feeling by 6 or 7 expert evaluators.
B: Evaluated "low" in film feeling by 4 or 5 expert evaluators.
C: Evaluated "low" in film feeling by 3 or fewer expert evaluators.

(2) Ease of Makeup Fixing

The ease of makeup fixing was determined depending on whether or not a face powder would be evenly applied with ease when each water-in-oil emulsified cosmetic was used, sebum was removed 5 hours later with a piece of oil blotting paper, and the face powder was then put on to fix the makeup. By the 10 expert evaluators, the ease of makeup fixing was evaluated on the basis of whether or not it is easy to adhere uniformly the face powder to the skin. Ranking was performed in accordance with the following standards.

A+: Evaluated "easy" to fix the makeup by 8 or more expert evaluators.
A: Evaluated "easy" to fix the makeup by 6 or 7 expert evaluators.
B: Evaluated "easy" to fix the makeup by 4 or 5 expert evaluators.
C: Evaluated "easy" to fix the makeup by 3 or fewer expert evaluators.

TABLE 3

| Components (wt. %) | Examples | | | | | | | |
|---|---|---|---|---|---|---|---|---|
| | 13 | 14 | 15 | 16 | 17 | 18 | 19 | 20 |
| Silicone dendrimer-acrylate copolymer*[1] | 10.0 | 16.7 | 33.3 | 10.0 | 16.7 | 6.7 | 3.3 | 10.0 |
| Dimethylpolysiloxane-polyoxyethylene copolymer*[2] | 0.4 | 0.4 | 0.4 | | | 0.4 | 0.4 | |
| Dimethylpolysiloxane-polyoxyethylene copolymer*[12] | | | | 2.2 | 2.2 | | | |
| Dimethylpolysiloxane-polyoxyethylene-polyoxypropylene copolymer*[13] | | | | | | | | 0.4 |
| Glyceryl-ether-modified silicone*[14] | 0.1 | 0.1 | 0.1 | 0.1 | 0.1 | 0.1 | 0.1 | 0.1 |
| 2-Ethylhexyl paramethoxycinnamate*[3] | 3.0 | 3.0 | 2.0 | 3.0 | 3.0 | | 3.0 | 3.0 |
| Diglyceryl monoisostearate*[15] | | | | | | 0.5 | | |
| Decamethylcyclopentasiloxane | 7.5 | 0.8 | | 5.7 | | 13.3 | 14.2 | 7.5 |
| Dimethylpolysiloxane (2 cs) | 10.0 | 10.0 | 10.0 | 10.0 | 9.0 | 10.0 | 10.0 | 10.0 |
| Dimethylpolysiloxane (6 cs) | 6.0 | 6.0 | 6.0 | 6.0 | 6.0 | 6.0 | 6.0 | 6.0 |
| Glycerin | 3.0 | 3.0 | 3.0 | 3.0 | 3.0 | 3.0 | 3.0 | 3.0 |
| Ethanol | 8.0 | 8.0 | 8.0 | 8.0 | 8.0 | 8.0 | 8.0 | 8.0 |
| Magnesium sulfate | 0.5 | 0.5 | 0.5 | 0.5 | 0.5 | 0.5 | 0.5 | 0.5 |
| Purified water | Balance | Balance | Balance | Balance | Balance | Balance | Balance | Balance |
| Silicone-treated fine particulate zinc oxide ("MZ504R3M", Tayka Corporation)*[8] (average particle size: 1.2 μm) | 2.0 | 2.0 | 2.0 | 2.0 | 2.0 | 2.0 | 2.0 | 2.0 |
| Silicone-treated fine particulate titanium dioxide ("MT600B", Tayka Corporation)*[8] (average particle size: 0.05 μm) | 1.5 | 1.5 | 1.5 | 1.5 | 1.5 | 1.5 | 1.5 | 1.5 |
| Silicone-treated titanium dioxide*[8] (average particle size: 0.2 μm) | 6.3 | 6.3 | 6.3 | 6.3 | 6.3 | 6.3 | 6.3 | 6.3 |
| Silicone-treated iron oxide (red, yellow, black)*[8] (average particle size: 0.4 μm) | 1.8 | 1.8 | 1.8 | 1.8 | 1.8 | 1.8 | 1.8 | 1.8 |
| Silicone-treated, iron-oxide-coated, titanated mica*[8] ("COLORONA ORIENTAL BEIGE", Merck & Co., Inc., average particle size: 7 μm) | 1.5 | 1.5 | 1.5 | 1.5 | 1.5 | 1.5 | 1.5 | 1.5 |
| Talc*[16] (average particle size: 17 μm) | 3.0 | 3.0 | 3.0 | 3.0 | 3.0 | 3.0 | 3.0 | 3.0 |
| Nylon resin*[17] (average particle size: 5 μm) | 3.0 | 3.0 | 3.0 | 3.0 | 3.0 | 3.0 | 3.0 | 3.0 |
| Total | 100 | 100 | 100 | 100 | 100 | 100 | 100 | 100 |
| (A)/(B) weight ratio | 1.0 | 1.7 | 5.0 | 1.0 | 1.7 | 4.0 | 0.3 | 1.0 |
| (A)/(D) weight ratio | 7.5 | 12.5 | 25.0 | 1.4 | 2.3 | 5.0 | 2.5 | 7.5 |
| Particles of 2 μm or smaller (wt. %) | 11.6 | 11.6 | 11.6 | 11.6 | 11.6 | 11.6 | 11.6 | 11.6 |
| Feel upon use (film feeling) | A+ | A | A | A+ | A+ | A | A+ | A |
| Concealment of pores shortly after application | A+ | A+ | A+ | A+ | A+ | A | A | A+ |
| Concealment of pores after 5 hrs | A+ | A+ | A+ | A | A | A | A | A |
| Concealment of creases after 5 hrs | A+ | A+ | A | A | A+ | A | A | A |
| Ease of makeup fixing | A+ | A+ | A | A | A+ | A | A | A |

*[1]"FA4001CM" (Dow Corning Toray Co., Ltd); 30% decamethylcyclopentasiloxane solution
*[2]"SH3775M" (Dow Corning Toray Co., Ltd.); HLB: 5
*[12]"KF6015" (Shin-Etsu Chemical Co., Ltd.); HLB: 4.5
*[13]"FZ2233" (Dow Corning Toray Co., Ltd.); HLB: 2
*[14]Produced according to Example 7 of JP-A-5-112424
*[3]"PARSOL MCX" (DSM Nutrition Japan K.K.); SP value: 19.2
*[15]"COSMOL 41V" (The Nisshin Oilio Group, Ltd.); SP value: 21.7
*[8]Treated at 2 wt. % with methylhydrogenpolysiloxane
*[16]"FK-300S" (Yamaguchi Mica Co., Ltd.)
*[17]"SP-500" (Toray Industries, Inc.)

TABLE 4

| Components (wt. %) | Examples | | | Comparative Examples | | | |
|---|---|---|---|---|---|---|---|
| | 21 | 22 | 23 | 10 | 11 | 12 | 13 |
| Silicone dendrimer-acrylate copolymer*1 | 10.0 | 10.0 | 10.0 | | 0.7 | 53.3 | 10.0 |
| Acrylate-silicone copolymer*10 | | | | 10.0 | | | |
| Dimethylpolysiloxane-polyoxyethylene copolymer*2 | 0.4 | 7.0 | | 0.4 | 0.4 | 0.4 | 0.4 |
| Glyceryl-ether-modified silicone*14 | 0.1 | 0.1 | 0.5 | 0.1 | 0.1 | 0.1 | 0.1 |
| 2-Ethylhexyl paramethoxycinnamate*3 | 3.0 | 3.0 | 3.0 | 3.0 | 3.0 | 3.0 | |
| Decamethylcyclopentasiloxane | 7.5 | 0.9 | 7.5 | 7.5 | 16.8 | | 10.5 |
| Dimethylpolysiloxane (2 cs) | 10.0 | 10.0 | 10.0 | 10.0 | 10.0 | 10.0 | 10.0 |
| Dimethylpolysiloxane (6 cs) | 6.0 | 6.0 | 6.0 | 6.0 | 6.0 | 6.0 | 6.0 |
| Glycerin | 3.0 | 3.0 | 3.0 | 3.0 | 3.0 | 3.0 | 3.0 |
| Ethanol | 8.0 | 8.0 | 8.0 | 8.0 | 8.0 | 8.0 | 8.0 |
| Magnesium sulfate | 0.5 | 0.5 | 0.5 | 0.5 | 0.5 | 0.5 | 0.5 |
| Purified water | Balance | Balance | Balance | Balance | Balance | Balance | Balance |
| Silicone-treated fine particulate zinc oxide ("MZ504R3M", Tayka Corporation)*8 (average particle size: 1.2 μm) | 2.0 | 2.0 | 2.0 | 2.0 | 2.0 | 2.0 | 2.0 |
| Silicone-treated fine particulate titanium dioxide ("MT600B", Tayka Corporation)*8 (average particle size: 0.05 μm) | 1.5 | 1.5 | 1.5 | 1.5 | 1.5 | 1.5 | 1.5 |
| Silicone-treated titanium dioxide*8 (average particle size: 0.2 μm) | 8.1 | 6.3 | 6.3 | 6.3 | 6.3 | 6.3 | 6.3 |
| Silicone-treated iron oxide (red, yellow, black)*8 (average particle size: 0.4 μm) | | 1.8 | 1.8 | 1.8 | 1.8 | 1.8 | 1.8 |
| Silicone-treated, iron-oxide-coated, titanated mica*8 ("COLORONA ORIENTAL BEIGE", Merck & Co., Inc., average particle size: 7 μm) | | 1.5 | 1.5 | 1.5 | 1.5 | 1.5 | 1.5 |
| Talc*16 (average particle size: 17 μm) | 4.5 | 3.0 | 3.0 | 3.0 | 3.0 | 3.0 | 3.0 |
| Nylon resin*17 (average particle size: 5 μm) | 3.0 | 3.0 | 3.0 | 3.0 | 3.0 | 3.0 | 3.0 |
| Total | 100 | 100 | 100 | 100 | 100 | 100 | 100 |
| (A)/(B) weight ratio | 1.0 | 1.0 | 1.0 | — | 0.1 | 5.3 | — |
| (A)/(D) weight ratio | 7.5 | 0.4 | — | — | 0.5 | 40.0 | 7.5 |
| Particles of 2 μm or smaller (wt. %) | 11.6 | 11.6 | 11.6 | 11.6 | 11.6 | 11.6 | 11.6 |
| Feel upon use (film feeling) | A+ | A | A | B | A | C | B |
| Concealment of pores shortly after application | B | B | A | B | B | C | B |
| Concealment of pores after 5 hrs | B | B | B | C | C | C | C |
| Concealment of creases after 5 hrs | B | B | B | C | C | C | C |
| Ease of makeup fixing | C | C | C | C | C | C | C |

*1"FA4001CM" (Dow Corning Toray Co., Ltd); 30% decamethylcyclopentasiloxane solution
*10"KP-545" (Shin-Etsu Chemical Co., Ltd.); 30% decamethylcyclopentasiloxane solution
*2"SH3775M" (Dow Corning Toray Co., Ltd.); HLB: 5
*14Produced according to Example 7 of JP-A-5-112424
*3"PARSOL MCX" (DSM Nutrition Japan K.K.); SP value: 19.2
*8Treated at 2 wt. % with methylhydrogenpolysiloxane
*16"FK-300S" (Yamaguchi Mica Co., Ltd.)
*17"SP-500" (Toray Industries, Inc.)

Example 24

Liquid Foundation

| | | |
|---|---|---|
| (1) | Silicone dendrimer-acrylate copolymer ("FA4001CM", 30% decamethylcyclopentasiloxane solution, product of Dow Corning Toray Co., Ltd.) | 6.7 (wt. %) |
| (2) | Dimethylpolysiloxane-polyoxyethylene copolymer ("SH3775M", Dow Corning Toray Silicone Co., Ltd.; HLB 5) | 0.8 |
| (3) | Glyceryl-ether-modified silicone | 0.2 |
| (4) | Acetyl tributyl citrate ("TRIBUTYL o-ACETYLCITRATE", product Of Wako Pure Chemical Industries, Ltd.; SP value: 20.1) | 0.5 |
| (5) | Decamethylcyclopentasiloxane | 15 |
| (6) | Dimethylpolysiloxane (2 cs) | 10 |
| (7) | Dimethylpolysiloxane (6 cs) | 3 |
| (8) | Glycerin | 2 |
| (9) | Ethanol | 2 |
| (10) | Magnesium sulfate | 0.5 |
| (11) | Purified water | Balance |
| (12) | Silicone-treated fine particulate zinc oxide ("MZ504R3M", Tayka Corporation; average particle size: 1.2 μm) | 2 |
| (13) | Silicone-treated fine particulate titanium dioxide ("MT600B", Tayka Corporation; average particle size: 0.05 μm) | 2 |
| (14) | Silicone-treated titanium dioxide (average particle size: 0.2 μm) | 8 |
| (15) | Silicone-treated iron oxide (red, yellow, black) (average particle size: 0.4 μm) | 2 |
| (16) | Silicone-treated, iron-oxide-coated, titanated mica ("COLORONA ORIENTAL BEIGE", Merck & Co., Inc., average particle size: 7 μm) | 10 |

-continued

| | | |
|---|---|---|
| (17) | Talc (average particle size: 17 µm) | 3 |
| (18) | Nylon resin (average particle size: 5 µm) | 3 |
| | Total | 100 |

(Procedure)

Each target water-in-oil emulsified foundation was obtained by uniformly mixing the components (1) to (7), dispersing the components (12) to (18) by a vacuum emulsifying mixer, and gradually adding a mixture of the components (8) to (11) thereinto while stirring, whereby the resultant mixture was emulsified. Thus, each target water-in-oil emulsified foundation was obtained.

$((A)/(B)=4.0)$ $((A)/(D)=2.51)$ (Particles of 2 µm or Smaller: 14 Wt. %)

Example 25

Creamy Foundation

| | | |
|---|---|---|
| (1) | Silicone dendrimer-acrylate copolymer ("FA4002ID", 40% isododecane solution, product of Dow Corning Toray Co., Ltd.) | 10 (wt. %) |
| (2) | Dimethylpolysiloxane-polyoxyethylene copolymer ("SH3772M", Dow Corning Toray Co., Ltd.; HLB 6) | 3 |
| (3) | Isododecane | 5 |
| (4) | Dimethylpolysiloxane (2 cs) | 10 |
| (5) | 2-Ethylhexyl paramethoxycinnamate ("PARSOL MCX, DSM Nutrition Japan K.K.; SP value: 19.2) | 1 |
| (6) | Silicone-treated titanium dioxide (average particle size: 0.2 µm) | 7 |
| (7) | Silicone-treated iron oxide (red, yellow, black) (average particle size: 0.4 µm) | 2 |
| (8) | Talc ("FK-300S", Yamaguchi Mica Co., Ltd.; average particle size: 17 µm) | 8 |
| (9) | Ethanol | 2 |
| (10) | Glycerin | 5 |
| (11) | Purified water | Balance |

(Procedure)

After the components (1) to (5) were uniformly mixed, the components (6) to (8) were dispersed by a vacuum emulsifying mixer. Into the dispersion, a mixture of the components (9) to (11) was gradually added and emulsified while stirring to obtain the target water-in-oil emulsified foundation.

$((A)/(B)=4)$ $((A)/(D)=1.33)$ (Particles of 2 µm and Smaller: 9 Wt. %)

The water-in-oil emulsified cosmetics obtained in Examples 24 and 25 were each good in a feel upon use, were each able to form an even cosmetic film on the skin, were each low in film feeling after applied to the skin, and were each excellent in adhesion to the skin and also in the effects that make fine wrinkles and pores hardly visible. Further, they were each good in the long-lasting property of makeup, and were each able to keep pores and creases hardly visible with time. Further, they each allowed easy fixing of makeup.

Synthesis Example 1

Synthesis of Flaky Powder of Zinc Oxide

Zinc sulfate ($1.6 \times 10^{-1}$ mole), sodium sulfate ($3.8 \times 10^{-2}$ mole), and as a trace element salt, ferrous sulfate ($1.6 \times 10^{-4}$ mole) were dissolved in a $5 \times 10^{-2}$ mole aqueous solution of sulfuric acid (315 mL). While stirring the solution at 6,000 rpm by a homomixer, a 2N aqueous solution of sodium hydroxide (230 mL) was charged over 15 seconds (pH: 12.8) to form a precipitate, and stirring was then continued for 10 minutes. Subsequently, aging was conducted at 100° C. for 90 minutes. Solid matter was collected by filtration, washed with water, and then dried at 230° C. for about 10 hours to obtain flake zinc oxide particles. The thus-obtained particles had an average particle size of 0.25 µm, an average particle thickness of 0.02 µm, and an average plate ratio of 13.

Examples 26-32 and Comparative Examples 14-15

Water-in-oil emulsified foundations of the formulations shown in Table 5 were produced, and in the similar evaluation method as the foregoing, were then evaluated for a feel upon use (film feeling), the concealment of pores shortly after application, the concealment of pores 5 hours after application, and the concealment of creases 5 hours after application, and were also evaluated for a moist feel and a feel of transparency. The results are shown together in Table 5.

(Procedure)

Each target water-in-oil emulsified foundation was obtained by mixing uniformly the oil-phase components and polymer components (the components (1) to (9)), dispersing the powder components (the components (14) to (22)) in the oil-phase components by a vacuum emulsifying mixer, and then gradually adding a mixture of the water-phase components (the components (10) to (13)) into the dispersion while stirring, whereby the resultant mixture was emulsified.

(Evaluation Methods)

(1) Moist Feel

By the 10 expert evaluators, a sensory evaluation of a moist feel was performed when each water-in-oil emulsified cosmetic was used. The evaluation results were ranked in accordance with the following standards.

$A^+$: Evaluated "moist" by 8 or more expert evaluators.

A: Evaluated "moist" by 6 or 7 expert evaluators.

B: Evaluated "moist" by 4 or 5 expert evaluators.

C: Evaluated "moist" by 3 or fewer expert evaluators.

(2) Feel of Transparency

By the 10 expert evaluators, a sensory evaluation of a feel of transparency shortly after application was performed when each water-in-oil emulsified cosmetic was used. The evaluation results were ranked in accordance with the following standards.

$A^+$: Evaluated "to have a feel of transparency" by 8 or more expert evaluators.

A: Evaluated "to have a feel of transparency" by 6 or 7 expert evaluators.

B: Evaluated "to have a feel of transparency" by 4 or expert evaluators.

C: Evaluated "to have a feel of transparency" by 3 or fewer expert evaluators.

TABLE 5

| Components (wt. %) | | | Examples | | | | | | | Comp. Exs. | |
|---|---|---|---|---|---|---|---|---|---|---|---|
| | | | 26 | 27 | 28 | 29 | 30 | 31 | 32 | 14 | 15 |
| 1 | A | Silicone dendrimer-acrylate copolymer*[1] | 16.7 | | 16.7 | 16.7 | 16.7 | 16.7 | 16.7 | | |
| 2 | A | Silicone dendrimer-acrylate copolymer*[18] | | 12.5 | | | | | | | |
| 3 | | Trimethylsiloxysilicate*[11] | | | | | | | | | 10.0 |
| 4 | | Dimethylpolysiloxane-polyoxyethylene copolymer*[19] | 0.4 | 0.4 | 0.4 | 0.4 | 0.4 | 0.4 | 0.4 | 0.4 | 0.4 |
| 5 | | Glyceryl-ether-modified silicone*[14] | 0.1 | 0.1 | 0.1 | 0.1 | 0.1 | 0.1 | 0.1 | 0.1 | 0.1 |
| 6 | | 2-Ethylhexyl paramethoxycinnamate*[3] | 3.0 | 3.0 | 3.0 | 3.0 | 3.0 | 3.0 | 3.0 | 3.0 | 3.0 |
| 7 | | Decamethylcyclopentasiloxane | 0.8 | | 0.8 | 0.8 | 0.8 | 0.8 | 0.8 | 17.5 | 7.5 |
| 8 | | Dimethylpolysiloxane (2 cs) | 10.0 | 10.0 | 10.0 | 10.0 | 10.0 | 10.0 | 10.0 | 10.0 | 10.0 |
| 9 | | Dimethylpolysiloxane (6 cs) | 6.0 | 6.0 | 6.0 | 6.0 | 6.0 | 6.0 | 6.0 | 6.0 | 6.0 |
| 10 | | Glycerin | 3.0 | 3.0 | 3.0 | 3.0 | 3.0 | 3.0 | 3.0 | 3.0 | 3.0 |
| 11 | | Ethanol | 8.0 | 8.0 | 8.0 | 8.0 | 8.0 | 8.0 | 8.0 | 8.0 | 8.0 |
| 12 | | Magnesium sulfate | 0.5 | 0.5 | 0.5 | 0.5 | 0.5 | 0.5 | 0.5 | 0.5 | 0.5 |
| 13 | | Purified water | Balance | Balance | Balance | Balance | Balance | Balance | Balance | Balance | Balance |
| 14 | E | Flaky powder of zinc oxide (Synthesis Example 1) | 3.0 | 3.0 | 7.0 | 0.5 | | | | 3.0 | 3.0 |
| 15 | E | Flaky powder of zinc oxide*[20] | | | | | 3.0 | | | | |
| 16 | | Silicone-treated fine particulate zinc oxide*[7] | | | | | | 3.0 | | | |
| 17 | | Talc*[21] | | | | | | | 3.0 | | |
| 18 | | Silicone-treated fine particulate titanium dioxide ("MT600B", Tayka Corporation)*[8] | 1.5 | 1.5 | 1.5 | 1.5 | 1.5 | 1.5 | 1.5 | 1.5 | 1.5 |
| 19 | | Silicone-treated titanium dioxide*[8] | 6.3 | 6.3 | 6.3 | 6.3 | 6.3 | 6.3 | 6.3 | 6.3 | 6.3 |
| 20 | | Silicone-treated iron oxide (red, yellow, black)*[8] | 1.8 | 1.8 | 1.8 | 1.8 | 1.8 | 1.8 | 1.8 | 1.8 | 1.8 |
| 21 | | Nylon resin*[17] | 3.0 | 3.0 | 3.0 | 3.0 | 3.0 | 3.0 | 3.0 | 3.0 | 3.0 |
| 22 | | Silicone-treated titanium dioxide-coated mica (violet interference light system)*[8] ("FLAMENCO SATIN VIOLET", BASF SE, average particle size: 8 μm) | 1.5 | 1.5 | 1.5 | 1.5 | 1.5 | 1.5 | 1.5 | 1.5 | 1.5 |
| Total | | | 100 | 100 | 100 | 100 | 100 | 100 | 100 | 100 | 100 |
| (A)/(E) weight ratio | | | 1.67 | 1.67 | 0.71 | 10 | 1.67 | — | ∞ | 0 | 0 |
| Moist feel | | | A⁺ | A⁺ | A | A | A | C | C | B | C |
| Feel upon use (film feeling) | | | A⁺ | A | A | A⁺ | A | A | A | A⁺ | B |
| Concealment of pores shortly after application | | | A⁺ | A⁺ | A⁺ | A | A⁺ | A⁺ | A⁺ | C | B |
| Feel of transparency | | | A⁺ | A⁺ | A | A⁺ | A | B | B | B | C |
| Concealment of pores after 5 hrs | | | A⁺ | A⁺ | A⁺ | A | A⁺ | A⁺ | A⁺ | C | C |
| Concealment of creases after 5 hrs | | | A⁺ | A⁺ | A⁺ | A⁺ | A⁺ | A⁺ | A⁺ | C | C |

*[1]"FA4001CM" (Dow Corning Toray Co., Ltd); 30% decamethylcyclopentasiloxane solution
*[18]"FA4002ID" (Dow Corning Toray Co., Ltd.); 40% isododecane solution
*[11]"KF-7312J" (Shin-Etsu Chemical Co., Ltd.); 50% decamethylcyclopentasiloxane solution
*[19]"SH3775M" (Dow Corning Toray Co., Ltd.)
*[14]Produced according to Example 7 of JP-A-5-112424
*[3]"PARSOL MCX" (DSM Nutrition Japan K.K.); SP value: 19.2
*[20]"LUXELEN FZT-400" (Sumitomo Chemical Co., Ltd.); average particle size: 5 μm, thickness: 0.2 μm, average plate ratio: 25
*[7]"MZ504R3M" (Tayka Corporation); 0.02 μm
*[21]"TALC JA-46R" (Asada Milling Co., Ltd.)
*[8]Treated at 2 wt. % with methylhydrogenpolysiloxane
*[17]"SP-500" (Toray Industries, Inc.)

Example 33

Make Up Base (Oil-Based Cosmetic)

(A)/(B)=0.3

A make up base (oil-based cosmetic) of the below-described formulation was produced by a usual procedure.
(Components)

| | | |
|---|---|---|
| (1) | Dimethylpolysiloxane-polyoxyethylene copolymer ("FZ2233", Dow Corning Toray Co., Ltd.) | 0.5 (wt. %) |
| (2) | Silicone dendrimer-acrylate copolymer ("FA4001CM", product of Dow Corning Toray Silicone Co., Ltd.; 30% decamethylcyclopentasiloxane solution) | 10.0 |

-continued

| | | |
|---|---|---|
| (3) | 2-Ethylhexyl paramethoxycinnamate ("PARSOL MCX, DSM Nutrition Japan K.K.; SP value: 19.2) | 10.0 |
| (4) | Decamethylcyclopentasiloxane | Balance |
| (5) | Dimethylpolysiloxane (2 cs) | 17.5 |
| (6) | Fluorine-modified silicone (the compound described in Example 4 of JP-A-6-184312) | 10.0 |
| (7) | Flaky powder of zinc oxide (Synthesis Example 1) | 5.0 |
| (8) | Talc | 9.2 |
| (9) | Mica | 9.2 |
| (10) | Fluorine compound-treated glass flakes containing fine titanium dioxide | 1.3 |
| (11) | Fluorine compound-treated iron oxide coated titanated mica | 2.6 |

-continued

| | | |
|---|---|---|
| (12) | Fluorine compound-treated iron oxide | 0.1 |
| (13) | Fluorine compound-treated urethane powder | 1.3 |
| (14) | Fluorine compound-treated nylon powder (treated at 5 wt. % with perfluoroalkylphosphate) | 1.3 |
| | Total | 100 |

The cosmetic obtained in Example 33 provided a moist feel and covering power, and was excellent in the texture of a finish.

Examples 34-42 and Comparative Examples 16-17

Water-in-oil emulsified foundations of the formulations shown in Table 6 were produced, and in the similar evaluation method as the foregoing, were then evaluated for a feel upon use (Film feeling), the concealment of pores shortly after application, the concealment of pores 5 hours after application, and the concealment of creases 5 hours after application, and were also evaluated for a finish with an adhesion feel. The results are shown together in Table 7.

(Procedure)
Each target water-in-oil emulsified foundation was obtained by uniformly mixing the oil-phase components and polymer components, dispersing the powder components in the oil-phase components by a propeller mixer, gradually adding a mixture of the water-phase components while stirring, performing emulsification by a homomixer, and then defoaming the emulsion.

(Evaluation Method)
(1) Finish with an Adhesion Feel Shortly after Application
By the 10 expert evaluators, a sensory evaluation of a finish with an adhesion feel shortly after application was performed when each water-in-oil emulsified cosmetic was used. The evaluation results were ranked in accordance with the following standards.
$A^+$: Evaluated to be "a finish with an adhesion feel" by 8 or more expert evaluators.
A: Evaluated to be "a finish with an adhesion feel" by 6 or 7 expert evaluators.
B: Evaluated to be "a finish with an adhesion feel" by 4 or 5 expert evaluators.
C: Evaluated to be "a finish with an adhesion feel" by 3 or fewer expert evaluators.

TABLE 6

| | | Examples | | | | | |
|---|---|---|---|---|---|---|---|
| | Components (wt. %) | 34 | 35 | 36 | 37 | 38 | 39 |
| (A) | Silicone dendrimer-acrylate copolymer; 30% D5 solution*1 | 11.7 | 5.0 | 5.0 | 2.1 | 11.7 | 11.7 |
| | (Amount of the polymer in the solution) | 3.5 | 1.5 | 1.5 | 0.64 | 3.5 | 3.5 |
| | Silicone dendrimer-acrylate copolymer; 40% isododecane solution*18 | | | | | | |
| | (Amount of the polymer in the solution) | | | | | | |
| | Trimethylsiloxysilicate; 50% D5 solution*11 | | | | | | |
| | (Amount of the polymer in the solution) | | | | | | |
| (F) | Poly(N-acylalkyleneimine)-modified silicone*22 | 1.5 | 1.5 | 1.5 | 1.5 | 4.0 | 0.24 |
| | Sugar-modified silicone*23 | | | | | | |
| (B) | 2-Ethylhexyl paramethoxycinnamate*3 | 3.0 | 3.0 | 2.1 | 0.9 | 3.0 | 3.0 |
| (G) | Decamethylcyclopentasiloxane (total amount) | 9.0 | 11.0 | 11.0 | 11.9 | 9.0 | 9.0 |
| | (including the solvent brought in with the components (A)) | 8.2 | 3.5 | 3.5 | 1.5 | 8.2 | 8.2 |
| | Isododecane (total amount) | — | — | — | — | — | — |
| | (including the solvent brought in with the component (A)) | | | | | | |
| | Dimethylpolysiloxane (2 cs) (total amount) | 10.0 | 10.0 | 10.0 | 10.0 | 10.0 | 10.0 |
| Oil | Dimethylpolysiloxane (6 cs) | 7.0 | 7.0 | 7.0 | 7.0 | 7.0 | 7.0 |
| phases | Dimethylpolysiloxane-polyoxyethylene copolymer*19 | 0.7 | 0.7 | 0.7 | 0.7 | 0.7 | 0.7 |
| Water | Magnesium sulfate | 0.5 | 0.5 | 0.5 | 0.5 | 0.5 | 0.5 |
| phases | Purified water | Balance | Balance | Balance | Balance | Balance | Balance |
| | Ethanol | 6.0 | 6.0 | 6.0 | 6.0 | 6.0 | 6.0 |
| Powders | Silicone-treated fine particulate zinc oxide*7 | 2.0 | 2.0 | 2.0 | 2.0 | 2.0 | 2.0 |
| | Talc*21 | 3.0 | 3.0 | 3.0 | 3.0 | 3.0 | 3.0 |
| | Silicone-treated fine particulate titanium dioxide ("MT600B", Tayka Corporation)*8 | 1.5 | 1.5 | 1.5 | 1.5 | 1.5 | 1.5 |
| | Silicone-treated titanium dioxide*8 | 6.3 | 6.3 | 6.3 | 6.3 | 6.3 | 6.3 |
| | Silicone-treated iron oxide (red, yellow, black)*8 | 1.8 | 1.8 | 1.8 | 1.8 | 1.8 | 1.8 |
| | Nylon resin*17 | 3.0 | 3.0 | 3.0 | 3.0 | 3.0 | 3.0 |
| | Silicone-treated titanium dioxide coated mica (violet interference light system)*8 ("FLAMENCO SATIN VIOLET", BASF SE, average particle size: 8 μm) | 1.5 | 1.5 | 1.5 | 1.5 | 1.5 | 1.5 |
| Total | | 100 | 100 | 100 | 100 | 100 | 100 |

| | | Examples | | | Comp. Exs. | |
|---|---|---|---|---|---|---|
| | Components (wt. %) | 40 | 41 | 42 | 16 | 17 |
| (A) | Silicone dendrimer-acrylate copolymer; 30% D5 solution*1 | | 11.7 | 11.7 | | 11.7 |
| | (Amount of the polymer in the solution) | | 3.5 | 3.5 | | 3.5 |
| | Silicone dendrimer-acrylate copolymer; 40% isododecane solution*18 | 8.8 | | | | |
| | (Amount of the polymer in the solution) | 3.5 | | | | |
| | Trimethylsiloxysilicate; 50% D5 solution*11 | | | | 7.0 | |
| | (Amount of the polymer in the solution) | | | | 3.5 | |
| (F) | Poly(N-acylalkyleneimine)-modified silicone*22 | 1.5 | | | 1.5 | 1.5 |
| | Sugar-modified silicone*23 | | | 1.5 | | |

TABLE 6-continued

| | | | | | | | |
|---|---|---|---|---|---|---|---|
| (B) | 2-Ethylhexyl paramethoxycinnamate*3 | 3.0 | 3.0 | 3.0 | 3.0 | | |
| (G) | Decamethylcyclopentasiloxane (total amount) | — | 9.0 | 9.0 | 9.0 | 9.0 | |
| | (including the solvent brought in with the components (A)) | | 8.2 | 8.2 | 3.5 | 8.2 | |
| | Isododecane (total amount) | 9.0 | — | | | | |
| | (including the solvent brought in with the component (A)) | 5.3 | | | | | |
| | Dimethylpolysiloxane (2 cs) (total amount) | 10.0 | 10.0 | 10.0 | 10.0 | 10.0 | |
| Oil phases | Dimethylpolysiloxane (6 cs) | 7.0 | 7.0 | 7.0 | 7.0 | 7.0 | |
| | Dimethylpolysiloxane-polyoxyethylene copolymer*19 | 0.7 | 0.7 | 0.7 | 0.7 | 0.7 | |
| Water phases | Magnesium sulfate | 0.5 | 0.5 | 0.5 | 0.5 | 0.5 | |
| | Purified water | Balance | Balance | Balance | Balance | Balance | |
| | Ethanol | 6.0 | 6.0 | 6.0 | 6.0 | 6.0 | |
| Powders | Silicone-treated fine particulate zinc oxide*7 | 2.0 | 2.0 | 2.0 | 2.0 | 2.0 | |
| | Talc*21 | 3.0 | 3.0 | 3.0 | 3.0 | 3.0 | |
| | Silicone-treated fine particulate titanium dioxide ("MT600B", Tayka Corporation) *8 | 1.5 | 1.5 | 1.5 | 1.5 | 1.5 | |
| | Silicone-treated titanium dioxide*8 | 6.3 | 6.3 | 6.3 | 6.3 | 6.3 | |
| | Silicone-treated iron oxide (red, yellow, black)*8 | 1.8 | 1.8 | 1.8 | 1.8 | 1.8 | |
| | Nylon resin*17 | 3.0 | 3.0 | 3.0 | 3.0 | 3.0 | |
| | Silicone-treated titanium dioxide coated micaviolet interference light system)*8 ("FLAMENCO SATIN VIOLET", BASF SE, average particle size: 8 μm) | 1.5 | 1.5 | 1.5 | 1.5 | 1.5 | |
| Total | | 100 | 100 | 100 | 100 | 100 | |

TABLE 7

| | Examples | | | | | | | | | Comp. Exs. | |
|---|---|---|---|---|---|---|---|---|---|---|---|
| | 34 | 35 | 36 | 37 | 38 | 39 | 40 | 41 | 42 | 16 | 17 |
| (A)/(F) (weight ratio) | 2.3 | 1.0 | 1.0 | 0.4 | 0.9 | 14.6 | 2.3 | 2.3 | — | — | 2.3 |
| (A)/(B) (weight ratio) | 1.2 | 0.5 | 0.7 | 0.7 | 1.2 | 1.2 | 1.2 | 1.2 | 1.2 | — | — |
| Feel upon use (film feeling) | A+ | A+ | A | A | A | A | A | A | A | B | B |
| Finish with an adhesion feel shortly after application | A+ | A | A+ | A | A | A+ | A+ | A | B | C | C |
| Concealment of pores shortly after application | A+ | A | A | A | A+ | A+ | A+ | A | A | B | B |
| Concealment of pores after 5 hrs | A+ | A | A | A | A+ | A+ | A+ | A | A | C | C |
| Concealment of creases after 5 hrs | A+ | A+ | A | A | A | A | A+ | A | A | C | C |

*1 "FA4001CM" (Dow Corning Toray Co., Ltd); 30% decamethylcyclopentasiloxane solution
*18 "FA4002ID" (Dow Corning Toray Co., Ltd.); 40% isododecane solution
*11 "KF-7312J" (Shin-Etsu Chemical Co., Ltd.); 50% decamethylcyclopentasiloxane solution
*22 Synthesized according to Synthesis Example 9 of JP-B-3118192
*23 "DOW CORNING CE-8810 SUGAR SILICONE EMULSION" (Dow Corning Toray Co., Ltd.)
*3 "PARSOL MCX" (DSM Nutrition Japan K.K.); SP value: 19.2
*19 "SH3775M" (Dow Corning Toray Co., Ltd.)
*7 "MZ504R3M" (Tayka Corporation); 0.02 μm
*21 "TALC JA-46R" (Asada Milling Co., Ltd.)
*8 Treated at 2 wt. % with methylhydrogenpolysiloxane
*17 "SP-500" (Toray Industries, Inc.)

Example 43

Make Up Base Cream

| | | |
|---|---|---|
| (1) | Dimethylpolysiloxane-polyoxyethylene Copolymer ("SH3775M", product of Dow Corning Toray Co., Ltd.) | 0.5 (wt. %) |
| (2) | Decamethylcyclopentasiloxane | 23.0 |
| (3) | Dimethylpolysiloxane (2 cs) | 17.5 |
| (4) | Silicone dendrimer-acrylate copolymer ("FA4001CM", 30% decamethylcyclopentasiloxane solution; product of Dow Corning Toray Co., Ltd.) | 3.0 |
| (5) | Fluorine-modified silicone (the compound described in Example 4 of JP-A-6-184312) | 4.0 |
| (6) | 2-Ethylhexyl paramethoxycinnamate ("PARSOL MCX, DSM Nutrition Japan K.K.; SP value: 19.2) | 2.0 |
| (7) | Poly(N-propionylethyleneimine)-modified silicone (synthesized according to Preparation Example 9 of JP-B-3118192) | 1.2 |
| (8) | Ethanol | 9.8 |
| (9) | Tuberose polysaccharide solution | 5.0 |
| (10) | Magnesium sulfate | 0.3 |
| (11) | Purified water | Balance |
| (12) | Talc | 3.0 |
| (13) | Mica | 3.0 |
| (14) | Silicone-treated titanium dioxide coated glass flakes | 2.0 |
| (15) | Silicone-treated, titanated mica | 2.0 |
| (16) | Fluorine compound-treated iron oxide | 0.045 |
| (17) | Fluorine compound-treated urethane powder | 2.0 |
| Total | | 100 |

(Procedure)

The components (1) to (7) were uniformly mixed, and the components (12) to (17) were then mixed by using a vacuum emulsifying mixer. Into the mixture, a mixture of the components (8) to (11) was added, followed by mixing to obtain a make up base cream.

$((A)/(B))=0.45$ $((A)/(F))=0.75$

Example 44

Creamy Foundation

| (1) | Silicone-treated titanium dioxide | 10.0 (wt. %) |
|---|---|---|
| (2) | Silicone-treated sericite | 8.0 |
| (3) | Silicone-treated red iron oxide | 2.0 |
| (4) | Silicone-treated yellow iron oxide | 3.5 |
| (5) | Silicone-treated black iron oxide | 0.5 |
| (6) | Poly(N-propionylethyleneimine)-modified Silicone (synthesized following Preparation Example 8 of JP-B-3118192) | 3.0 |
| (7) | Silicone dendrimer-acrylate copolymer ("FA4002ID", 40% isododecane solution, product of Dow Corning Toray Co., Ltd.) | 10.0 |
| (8) | Decamethylcyclopentasiloxane | 15.0 |
| (9) | Dimethylpolysiloxane-methylpolyoxyethylene copolymer ("KF-6015", product of Shin-Etsu Chemical Co., Ltd.) | 4.0 |
| (10) | Dimethylpolysiloxane (2 cs) | 1.0 |
| (11) | 2-Ethylhexyl paramethoxycinnamate ("PARSOL MCX, DSM Nutrition Japan K.K.; SP value: 19.2) | 10.0 |
| (12) | Ethanol | 7.0 |
| (13) | Glycerin | 5.0 |
| (14) | Purified water | Balance |
| | Total | 100 |

(Procedure)

The components (6) to (11) were uniformly mixed, and the components (1) to (5) were dispersed therein by using a vacuum emulsifying mixer. Further, the components (12) to (14) were added, following by stirring to obtain a creamy foundation.

$((A)/(B))=4$ $((A)/(F))=1.33$

Example 45

Eye Shadow Composition

| (1) | Decamethyltetrasiloxane (1.5 cs) | Balance (wt. %) |
|---|---|---|
| (2) | Silicone dendrimer-acrylate copolymer ("FA4002ID", 40% isododecane solution, product of Dow Corning Toray Co., Ltd.) | 10 |
| (3) | Diisostearyl malate | 1 |
| (4) | Poly(N-propionylethyleneimine)-modified silicone (synthesized according to Preparation Example 9 of JP-B-3118192) | 3.6 |
| (5) | Ethanol | 8.4 |
| (6) | Dimethylpolysiloxane-methylpolyoxyethylene copolymer ("KF-6015", product of Shin-Etsu Chemical Co., Ltd.) | 6.0 |
| (7) | Purified water | 5.0 |
| (8) | Silicone-treated talc | 1.8 |
| (9) | Silicone-treated, titanated mica | 22.0 |
| | Total | 100 |

(Procedure)

The components (1) to (6) were uniformly mixed, and the components (8) to (9) were added thereto, followed by mixing by using a vacuum emulsifying mixer. Further, the component (7) was added, following by mixing to obtain an eye shadow composition.

$((A)/(B))=4$ $((A)/(F))=1.11$

Example 46

Suncare Foundation

| (1) | α-Monoisostearyl glyceryl ether | 2 (wt. %) |
|---|---|---|
| (2) | Aluminum distearate | 0.2 |
| (3) | Silicone dendrimer-acrylate copolymer ("FA4002ID", 40% isododecane solution, product of Dow Corning Toray Co., Ltd.) | 10 |
| (4) | Neopentyl glycol dicaprate | 5 |
| (5) | Methylphenylpolysiloxane (14 cs) | 5 |
| (6) | 2-Ethylhexyl paramethoxycinnamate ("PARSOL MCX, DSM Nutrition Japan K.K.; SP value: 19.2) | 2.0 |
| (7) | Isododecane | 2.0 |
| (8) | Silicone-treated, fine particulate Titanium dioxide | 3.0 |
| (9) | Silicone-treated sericite | 2.0 |
| (10) | Silicone-treated talc | 3.0 |
| (11) | Silicone-treated red iron oxide | 0.4 |
| (12) | Silicone-treated yellow iron oxide | 0.7 |
| (13) | Silicone-treated black iron oxide | 0.1 |
| (14) | Poly(N-propionylethyleneimine)-modified silicone (synthesized according to Preparation Example 5 of JP-A-7-133352) | 2.0 |
| (15) | Magnesium sulfate | 1.0 |
| (16) | 70% Aqueous sorbitol solution | 5.0 |
| (17) | Methylparaben | 0.1 |
| (18) | Fragrance | Trace |
| (19) | Purified water | Balance |
| | Total | 100 |

(Procedure)

The components (1) to (13) were uniformly mixed, and were heated beforehand into a homogeneous solution. The components (14) to (19) were added thereto, followed by stirring and mixing it in an emulsion machine. The mixture was allowed to cool to room temperature to obtain a suncare foundation.

$((A)/(B))=0.6$ $((A)/(F))=2$

The cosmetics obtained in Examples 43 to 46 were all excellent in a feel upon use, finish and long-lasting property, especially in finish with an adhesion feel.

The invention claimed is:

1. A cosmetic composition comprising the following components (A), (B) and (C):
 (A) from 0.1 to 20 wt. % of a (meth)acrylate-based polymer having a carbosiloxane dendrimer structure in a side chain thereof, wherein the carbosiloxane dendrimer structure is a group represented by the following formula (1):

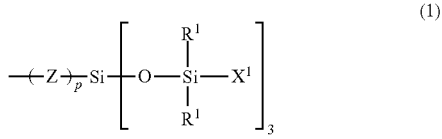

wherein Z is a divalent organic group, p is 1, $R^1$ is a methyl group, and $X^1$ is a silylalkyl group which, when i=1, is represented by the following formula (3):

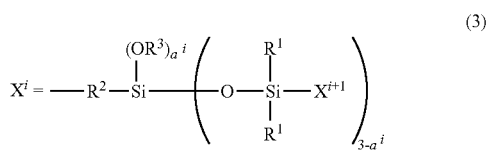

wherein $R^1$ is the same as defined above, $R^2$ is an ethylene group, a methylethylene group, a hexylene group, a 1-methylpentylene group or a 1,4-dimethylbutylene group, $R^3$ is an alkyl group having from 1 to 10 carbon atoms, and $X^{i+1}$ is a hydrogen atom or a methyl group, i is an integer of from 1 to 10 which represents the generation of the silylalkyl group, $a^i$ is 0, the divalent organic group as Z is the organic group represented by the following formula (2):

wherein R9 is an ethylene group or a propylene group,
 (B) from 0.1 to 20 wt. % of a nonvolatile cosmetic oil, which is in a liquid form at 25° C. and has a solubility parameter of 16.5 to 23, and a molecular weight ranging from 250 to 2,000, and
 (C) from 1 to 25 wt. % of a hydrophobic powder,
 wherein a weight ratio of the component (A) to the component (B), (A)/(B), is from 0.3 to 5.

2. The cosmetic composition according to claim 1, wherein a part or an entire part of the hydrophobic powder as the component (C) is a hydrophobic powder with iron oxide contained therein.

3. The cosmetic composition according to claim 1, further comprising:
 (D) from 0.1 to 6 wt. % of a polyether-modified silicone.

4. The cosmetic composition according to claim 3, wherein a weight ratio of the component (A) to the component (D), (A)/(D), is from 1.2 to 30.

5. The cosmetic composition according to claim 3 or 4, wherein the polyether-modified silicone as the component (D) is one having an HLB of from 1 to 6.

6. The cosmetic composition according to claim 1, further comprising:
 (E) flaky powder of zinc oxide having an average particle size of from 0.1 to 6 μm, an average particle thickness of from 0.01 to 0.3 μm, and an average plate ratio of 3 or greater.

7. The cosmetic composition according to claim 6, wherein a weight ratio of the component (A) to the component (E), (A)/(E), is from 0.05 to 20.

8. The cosmetic composition according to claim 1, further comprising:
 (F) a poly(N-acylalkyleneimine)-modified silicone and/or a sugar-modified silicone.

9. The cosmetic composition according to claim 1, wherein the (meth)acrylate-based polymer having a carbosiloxane dendrimer structure has the following formula:

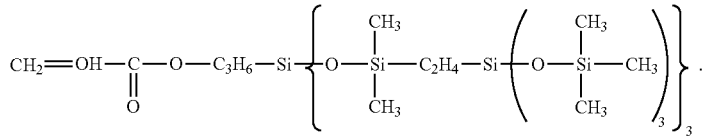

* * * * *